United States Patent
Muller et al.

(10) Patent No.: US 12,116,574 B2
(45) Date of Patent: Oct. 15, 2024

(54) ANTI-INFLAMMATORY TREATMENT VIA INHIBITION OF ENDOTHELIAL CELL KINESIN LIGHT CHAIN 1, VARIANT 1 (KLC1C)

(71) Applicant: Northwestern University, Evanston, IL (US)

(72) Inventors: William A. Muller, Evanston, IL (US); Bita F. Cyrus, Chicago, IL (US)

(73) Assignee: Northwestern University, Evanston, IL (US)

( * ) Notice: Subject to any disclaimer, the term of this patent is extended or adjusted under 35 U.S.C. 154(b) by 85 days.

(21) Appl. No.: 17/474,949

(22) Filed: Sep. 14, 2021

(65) Prior Publication Data

US 2022/0259591 A1    Aug. 18, 2022

Related U.S. Application Data

(63) Continuation of application No. 16/519,721, filed on Jul. 23, 2019, now Pat. No. 11,118,180, which is a continuation of application No. 15/401,794, filed on Jan. 9, 2017, now abandoned.

(60) Provisional application No. 62/276,503, filed on Jan. 8, 2016.

(51) Int. Cl.
| | |
|---|---|
| *C12N 15/113* | (2010.01) |
| *A61K 31/7105* | (2006.01) |
| *A61K 31/713* | (2006.01) |
| *A61K 38/00* | (2006.01) |
| *A61K 38/46* | (2006.01) |
| *A61K 45/06* | (2006.01) |

(52) U.S. Cl.
CPC ........ *C12N 15/113* (2013.01); *A61K 31/7105* (2013.01); *A61K 31/713* (2013.01); *A61K 38/005* (2013.01); *A61K 38/46* (2013.01); *A61K 45/06* (2013.01); *C12Y 306/04004* (2013.01); *C12Y 306/04005* (2013.01); *C12N 2310/14* (2013.01); *C12N 2310/531* (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 4,946,778 A | 8/1990 | Ladner et al. |
| 5,260,203 A | 11/1993 | Ladner et al. |
| 2008/0025958 A1 | 1/2008 | Hannon et al. |

FOREIGN PATENT DOCUMENTS

WO    WO 88/01649    3/1988

OTHER PUBLICATIONS

Wozniak et al. (The EMBO Journal (2006)25:5457-5468).*
Aizawa et al., Kinesin family in murine central nervous system. The Journal of cell biology 1992, 119:1287-96.
Allmendinger et al., Fluoroolefin dipeptide isosteres—I.: The synthesis of Glyψ(CF=CH)Gly and racemic Pheψy(CF=CH)Gly, Tetrahedron Lett., 1990, 31:7297-7300.
Anisman et al., Neuroimmune mechanisms in health and disease: 2. Disease. Cmaj 1996, 155:1075-82.
Bloom et al., Native structure and physical properties of bovine brain kinesin and identification of the ATP-binding subunit polypeptide. Biochemistry 1988, 27:3409-16.
Butcher, Leukocyte-endothelial cell recognition: three (or more) steps to specificity and diversity. Cell 1991, 67:1033-6.
Chorev et al., A dozen years of retro-inverso peptidomimetics, Acc. Chem. Res, 1993, 26:266-273.
Clackson et al., Making antibody fragments using phage display libraries, Nature, 1991, 352:624-628.
Cole et al., Novel heterotrimeric kinesin-related protein purified from sea urchin eggs. Nature 1993, 366:268-70.
Cyr et al., Molecular genetics of kinesin light chains: generation of isoforms by alternative splicing. Proceedings of the National Academy of Sciences of the United States of America 1991, 88:10114-8.
Daire et al., Kinesin-1 regulates microtubule dynamics via a c-Jun N-terminal kinase-dependent mechanism. The Journal of biological chemistry 2009, 284:31992-2001.
Diefenbach et al., The C-terminal region of the stalk domain of ubiquitous human kinesin heavy chain contains the binding site for kinesin light chain. Biochemistry 1998, 37:16663-70.
Feng et al., Segregation of VE-cadherin from the LBRC depends on the ectodomain sequence required for homophilic adhesion. Journal of cell science 2015, 128:576-88.
Feng et al., Vesiculo-vacuolar organelles and the regulation of venule permeability to macromolecules by vascular permeability factor, histamine, and serotonin. J Exp Med 1996, 183:1981-6.
Fundamental Immunology, 1989, Paul, W., ed., 2nd ed. Raven Press, N.Y, TOC only, 4 pages. Will provide specific pages upon Examiner request.
Gindhart et al., Kinesin light chains are essential for axonal transport in *Drosophila*. The Journal of cell biology 1998, 141:443-54.
Gindhart et al., Tetratrico peptide repeats are present in the kinesin light chain. Trends in biochemical sciences 1996, 21:52-3.
Glater et al., Axonal transport of mitochondria requires milton to recruit kinesin heavy chain and is light chain independent. The Journal of cell biology 2006, 173:545-57.
Gyoeva et al., An isoform of kinesin light chain specific for the Golgi complex. Journal of cell science 2000, 113 ( Pt 11): 2047-54.
Hirokawa et al., Kinesin superfamily motor proteins and intracellular transport. Nat Rev Mol Cell Biol 2009, 10:682-96.
Hirokawa et al., Submolecular domains of bovine brain kinesin identified by electron microscopy and monoclonal antibody decoration. Cell 1989, 56:867-78.

(Continued)

*Primary Examiner* — Kimberly Chong
(74) *Attorney, Agent, or Firm* — David W. Staple; Casimir Jones, S.C.

(57) ABSTRACT

Provided herein are compositions and methods for the inhibition of endothelial cell kinesin light chain 1, variant 1 (KLC1C) expression and/or activity, and treatment or prevention of inflammation therewith.

12 Claims, 17 Drawing Sheets

Specification includes a Sequence Listing.

(56) References Cited

OTHER PUBLICATIONS

Hirokawa, From electron microscopy to molecular cell biology, molecular genetics and structural biology: intracellular transport and kinesin superfamily proteins, KIFs: genes, structure, dynamics and functions. Journal of Electron Microscopy 2011, 60:S63-S92.
Hoffman et al., The Stereoselective Synthesis of 2-Alkyl .gamma.-Keto Acid and Heterocyclic Ketomethylene Peptide Isostere Core Units Using Chiral Alkylation by 2-Triflyloxy Esters, J. Org. Chem., 1995, 60:5107-5113.
Ingold et al., Inhibition of kinesin-driven microtubule motility by monoclonal antibodies to kinesin heavy chains. The Journal of cell biology 1988, 107:2657-67.
Inomata et al., A scaffold protein JIP-1b enhances amyloid precursor protein phosphorylation by JNK and its association with kinesin light chain 1. The Journal of biological chemistry 2003, 278:22946-55.
Jaulin et al., Polarization-dependent selective transport to the apical membrane by KIF5B in MDCK cells. Dev Cell 2007, 13:511-22.
Junco et al., Kinesin light-chain KLC3 expression in testis is restricted to spermatids. Biology of reproduction 2001, 64:1320-30.
Kamal et al., Axonal transport of amyloid precursor protein is mediated by direct binding to the kinesin light chain subunit of kinesin-I. Neuron 2000, 28:449-59.
Kanai et al., KIF5C, a novel neuronal kinesin enriched in motor neurons. J Neurosci 2000, 20:6374-84.
Khodjakov et al., A specific light chain of kinesin associates with mitochondria in cultured cells. Mol Biol Cell 1998, 9:333-43.
Kohler et al., Continuous cultures of fused cells secreting antibody of predefined specificity, Nature, 1975, 256:495-497.
Krylyshkina et al., Modulation of substrate adhesion dynamics via microtubule targeting requires kinesin-1. The Journal of cell biology 2002, 156:349-59.
Lavielle et al., Importance of the leucine side-chain to the spasmogenic activity and binding of substance P analogues, Int J Pept Protein Res. Sep. 1993;42(3):270-7.
Lawrence et al., A standardized kinesin nomenclature. J Cell Biol 2004, 167:19-22.
Ley et al., Getting to the site of inflammation: the leukocyte adhesion cascade updated. Nat Rev Immunol 2007, 7:678-89.
Liao et al., Migration of monocytes across endothelium and passage through extracellular matrix involve separate molecular domains of PECAM-1. J Exp Med 1995, 182:1337-43.
Liao, Kinesin is a candidate for cross-bridging microtubules and intermediate filaments. Selective binding of kinesin to detyrosinated tubulin and vimentin. J Biol Chem 1998, 273:9797-803.
Luisi et al., $\psi(SO_2\text{-NH})$ transition state isosteres of peptides. Synthesis of the glutathione disulfide analogue, Tetrahedron Lett. 1993, 34:2391-2392.
Luthman et al., Peptides and Petidomimetics, in Drug Design and Development, Chapter 14, Krogsgaard-Larsen, Liljefors and Madsen (Eds) 1996, Horwood Acad. pp. 386-406.
Mamdouh et al., Leukocyte transmigration requires kinesin-mediated microtubule-dependent membrane trafficking from the lateral border recycling compartment. J Exp Med 2008, 205:951-66.
Mamdouh et al., Targeted recycling of PECAM from endothelial cell surface-connected compartments during diapedesis. Nature 2003, 421:748-53.
Mamdouh et al., Transcellular migration of leukocytes is mediated by the endothelial lateral border recycling compartment. J Exp Med 2009, 206:2795-808.

Marks et al., By-passing immunization. Human antibodies from V-gene libraries displayed on phage, J. Mol. Biol., 1991, 222:581-597.
McCart et al., Alternatively spliced products of the human kinesin light chain 1 (KNS2) gene. Traffic 2003, 4:576-80.
Morihara et al., Transcriptome analysis of distinct mouse strains reveals kinesin light chain-1 splicing as an amyloid-beta accumulation modifier. Proceedings of the National Academy of Sciences of the United States of America 2014, 111:2638-43.
Muller et al., A human endothelial cell-restricted, externally disposed plasmalemmal protein enriched in intercellular junctions. J Exp Med 1989, 170:399-414.
Muller et al., Monocyte-selective transendothelial migration: Dissection of the binding and transmigration phases by an in vitro assay. J Exp Med 1992, 176:819-28.
Muller et al., PECAM-1 is required for transendothelial migration of leukocytes. J Exp Med 1993, 178:449-60.
Muller, Mechanisms of leukocyte transendothelial migration. Annu Rev Pathol 2011, 6:323-44.
Niclas et al., Cloning and localization of a conventional kinesin motor expressed exclusively in neurons. Neuron 1994, 12:1059-72.
Ostresh et al., "Libraries from libraries": chemical transformation of combinatorial libraries to extend the range and repertoire of chemical diversity, Proc Natl Acad Sci USA. Nov. 8, 1994;91(23):11138-42.
Rahman et al., Two kinesin light chain genes in mice. Identification and characterization of the encoded proteins. The Journal of biological chemistry 1998, 273:15395-403.
Rice et al., Paradigm lost: milton connects kinesin heavy chain to miro on mitochondria. The Journal of cell biology 2006, 173:459-61.
Rodionov et al., Kinesin is responsible for centrifugal movement of pigment granules in melanophores. Proc Natl Acad Sci U S A 1991, 88:4956-60.
Sasaki et al., Protection of $\psi(CH2NH)$ Peptide Bond with 2, 4-Dimethoxybenzyl Group in Solid-Phase Peptide Synthesis, J. Chem. Pharm. Bull., 1997, 45:13-17.
Schmidt et al., Structure-activity relationships of dermorphin analogues containing N-substituted amino acids in the 2-position of the peptide sequence, Int J Pept Protein Res. Jul. 1995;46(1):47-55.
Sherman et al., Compatibility of thioamides with reverse turn features: synthesis and conformational analysis of two model cyclic pseudopeptides containing thioamides as backbone modifications, J. Am. Chem. Soc., 1990, 112:433-441.
Spatola, Synthesis of Pseudopeptides, Methods Neurosci, 1993, 13:19-42.
Sullivan et al., Neutrophil and monocyte recruitment by PECAM, CD99, and other molecules via the LBRC. Seminars in immunopathology 2014, 36:193-209.
Sullivan et al., Poliovirus receptor (CD155) regulates a step in transendothelial migration between PECAM and CD99. Am J Pathol 2013, 182:1031-42.
Wedaman et al., Sequences of sea urchin kinesin light chain isoforms. Journal of molecular biology 1993, 231:155-8.
Woźniak et al., Cargo selection by specific kinesin light chain 1 isoforms. EMBO J 2006, 25:5457-68.
Wright et al., Identification of the C3bi receptor of human monocytes and macrophages by using monoclonal antibodies. Proceedings of the National Academy of Science 1983, 80:5699-703.
Zen et al., Leukocyte-epithelial interactions. Curr Opin Cell Biol 2003, 15:557-64.

* cited by examiner

Mouse IgG-Injected Monolayers

Adhesion

FIG. 2A

Resistant Kinesin-1 Construct

```
   1 ATGGCGGACC
  11 TGGCCGAGTG CAACATCAAA GTGATGTGTC GCTTCAGACC TCTCAACGAG TCTGAAGTGA
  71 ACCGCGGCGA CAAGTACATC GCCAAGTTTC AGGGAGAAGA CACGGTCGTG ATCGCGTCCA
 131 AGCCTTATGC ATTTGATCGG GTGTTCCAGT CAAGCACATC TCAGGAACAG GTCTATAATG
 251 ACTGTGCAAA GAAGATTGTT AAAGACGTCC TAGAGGGATA TAATGGAACA ATATTTGCAT
 311 ATGGACAAAC ATCCTCTGGG AAGACACACA CAATGGAGGG TAAACTTCAT GATCCAGAAG
 371 GCATGGGAAT TATTCCAAGA ATAGTGCAAG ATATTTTTAA TTATATTTAC TCCATGGATG
 431 AAAATTTGGA ATTTCATATT AAGGTTTCAT ATTTTGAAAT ATATTTGGAT AAGATAAGGG
 491 ACCTGTTAGA TGTTTCAAAG ACCAACCTTT CAGTTCATGA AGACAAAAAC CGAGTTCCCT
 551 ATGTAAAGGG GTGCACAGAG CGTTTTGTAT GTAGTCCAGA TGAAGTTATG GATACCATAG
 611 ATGAAGGAAA ATCCAACAGA CATGTAGCAG TTACAAATAT GAATGAACAT AGCTCTAGGA
 671 GTCACAGTAT ATTTCTTATT AATGTCAAAC AAGAGAACAC ACAAACGGAA CAAAAGCTGA
 731 GTGGAAAACT TTATCTGGTT GATTTAGCTG GTAGTGAAAA GGTTAGTAAA ACTGGAGCTG
 791 AAGGTGCTGT GCTGGATGAA GCTAAAAACA TCAACAAGTC ACTTTCTGCT CTTGGAAATG
 851 TTATTTCTGC TTTGGCTGAG GGTAGTACAT ATGTTCCATA TCGAGATAGT AAAATGACAA
 911 GAATCCTTCA AGATTCATTA GGTGGCAACT GTAGAACCAC TATTGTAATT TGCTGCTCTC
 971 CATCATCATA CAATGAGTCT GAAACAAAAT CTACACTCTT ATTTGGCCAA AGGGCCAAAA
1031 CAATTAAGAA CACAGTTTGT GTCAATGTGG AGTTAACTGC AGAACAGTGG AAAAAGAAGT
1091 ATGAAAAAGA AAAAGAAAAA AATAAGATCC TGCGGAACAC TATTCAGTGG CTTGAAAATG
1151 AGCTCAACAG ATGGCGTAAT GGGGAGACGG TGCCTATTGA TGAACAGTTT GACAAAGAGA
1211 AAGCCAACTT GGAAGCTTTC ACAGTGGATA AAGATATTAC TCTTACCAAT GATAAACCAG
1271 CAACCGCAAT TGGAGTTATA GGAAATTTTA CTGATGCTGA AGAAGAAAG TGTGAAGAAG
1331 AAATTGCTAA ATTATACAAA CAGCTTGATG ACAAGGATGA AGAAATTAAC CAGCAAAGTC
1391 AACTGGTAGA GAAACTGAAG ACGCAAATGT TGGATCAGGA GGAGCTTTTG GCATCTACCA
1451 GAAGGGATCA AGACAATATG CAAGCTGAGC TGAATCGCCT TCAAGCAGAA AATGATGCCT
1511 CTAAAGAAGA AGTGAAAGAA GTTTTACAGG CCCTAGAAGA ACTTGCTGTC AATTATGATC
1571 AGAAGTCTCA GGAAGTTGAA GACAAAACTA AGGAATATGA ATTGCTTAGT GATGAATTGA
1631 ATCAGAAATC GGCAACTTTA GCGAGTATAG ATGCTGAGCT TCAGAAACTT AAGGAAATGA
1691 CCAACCACCA GAAAAAACGA GCAGCTGAGA TGATGGCATC TTTACTAAAA GACCTTGCAG
1751 AAATAGGAAT TGCTGTGGGA AATAATGATG TAAAGCAGCC TGAGGGAACT GGCATGATAG
``` targeted sequences shown are mutated to be resistant to knockdown

FIG. 2B

Resistant Kinesin-1 Construct (cont.)

```
1811 ATGAAGAGTT CACTGTTGCA AGACTCTACA TTAGCAAAAT GAAGTCAGAA GTAAAAACCA
1871 TGGTGAAACG TTGCAAGCAG TTAGAAAGCA CACAAACTGA GAGCAACAAA AAAATGGAAG
1931 AAAATGAAAA GGAGTTAGCA GCATGTCAGC TTCGTATCTC TCAACATGAA GCCAAAATCA
1991 AGTCATTGAC TGAATACCTT CAAAATGTGG AACAAAAGAA AAGACAGTTG GAGGAATCTG
2051 TCGATGCCCT CAGTGAAGAA CTAGTCCAGC TTCGAGCACA AGAGAAAGTC CATGAAATGG
2111 AAAAGGAGCA CTTAAATAAG GTTCAGACTG CAAATGAAGT TAAGCAAGCT GTTGAACAGC
2171 AGATCCAGAG CCATAGAGAA ACTCATCAAA AACAGATCAG TAGTTTGAGA GATGAAGTAG
2231 AAGCAAAAGC AAAACTTATT ACTGATCTTC AAGACCAAAA CCAGAAAATG ATGTTAGAGC
2291 AGGAACGTCT AAGAGTAGAA CATGAGAAGT TGAAAGCCAC AGATCAGGAA AAGAGCAGAA
2351 AACTACATGA ACTTACGGTT ATGCAAGATA GACGAGAACA AGCAAGACAA GACTTGAAGG
2411 GTTTGGAAGA GACAGTGGCA AAAGAACTTC AGACTTTACA CAACCTGCGC AAACTCTTTG
2471 TTCAGGACCT GGCTACAAGA GTTAAAAAGA GTGCTGAGAT TGATTCTGAT GACACCGGAG
2531 GCAGCGCTGC TCAGAAGCAA AAAATCTCCT TTCTTGAAAA TAATCTTGAA CAGCTCACTA
2591 AAGTGCACAA ACAGTTGGTA CGTGATAATG CAGATCTCCG CTGTGAACTT CCTAAGTTGG
2651 AAAAGCGACT TCGAGCTACA GCTGAGAGAG TGAAAGCTTT GGAATCAGCA CTGAAAGAAG
2711 CTAAAGAAAA TGCATCTCGT GATCGCAAAC GCTATCAGCA AGAAGTAGAT CGCATAAAGG
2771 AAGCAGTCAG GTCAAAGAAT ATGGCCAGAA GAGGGCATTC TGCACAGATT GCTAAACCTA
2831 TTCGTCCCGG GCAACATCCA GCAGCTTCTC CAACTCACCC AAGTGCAATT CGTGGAGGAG
2891 GTGCATTTGT TCAGAACAGC CAGCCAGTGG CAGTGCGAGG TGGAGGAGGC AAACAAGTGT
2951 AA
``` targeted sequences shown are mutated to be resistant to knockdown

SEQUENCE LISTING

```
<160> NUMBER OF SEQ ID NOS: 13

<210> SEQ ID NO 1
<211> LENGTH: 139
<212> TYPE: PRT
<213> ORGANISM: Homo sapiens

<400> SEQUENCE: 1

Met His Ala Glu Glu Arg Glu Glu Cys Lys Gly Lys Gln Lys Asp Gly
1               5                   10                  15

Thr Ser Phe Gly Glu Tyr Gly Gly Trp Tyr Lys Ala Cys Lys Val Asp
            20                  25                  30

Ser Pro Thr Val Thr Thr Thr Leu Lys Asn Leu Gly Ala Leu Tyr Arg
        35                  40                  45

Arg Gln Gly Lys Phe Glu Ala Ala Glu Thr Leu Glu Glu Ala Ala Met
    50                  55                  60

Arg Ser Arg Lys Gln Arg Ser Ile Ser Glu Ile Pro Lys Lys Ile Leu
65                  70                  75                  80

Ser Ala Asn Gly Ser Asn His Phe Pro Leu Pro Gly Ser Gln Gly Leu
                85                  90                  95

Asp Asn Val His Lys Gln Arg Val Ala Glu Val Leu Asn Asp Pro Glu
            100                 105                 110

Asn Met Glu Lys Arg Arg Ser Arg Glu Ser Leu Asn Val Asp Val Val
        115                 120                 125

Lys Tyr Glu Ser Gly Pro Asp Gly Gly Glu Glu
    130                 135
```

<210> SEQ ID NO 2
<211> LENGTH: 10
<212> TYPE: PRT
<213> ORGANISM: Homo sapiens

<400> SEQUENCE: 2

Met Arg Lys Met Lys Leu Gly Leu Val Asn
1               5                   10

<210> SEQ ID NO 3
<211> LENGTH: 149
<212> TYPE: PRT
<213> ORGANISM: Homo sapiens

<400> SEQUENCE: 3

Met His Ala Glu Glu Arg Glu Glu Cys Lys Gly Lys Gln Lys Asp Gly
1               5                   10                  15

Thr Ser Phe Gly Glu Tyr Gly Gly Trp Tyr Lys Ala Cys Lys Val Asp
            20                  25                  30

Ser Pro Thr Val Thr Thr Thr Leu Lys Asn Leu Gly Ala Leu Tyr Arg
        35                  40                  45

Arg Gln Gly Lys Phe Glu Ala Ala Glu Thr Leu Glu Glu Ala Ala Met
    50                  55                  60

Arg Ser Arg Lys Gln Arg Ser Ile Ser Glu Ile Pro Lys Lys Ile Leu
65                  70                  75                  80

Ser Ala Asn Gly Ser Asn His Phe Pro Leu Pro Gly Ser Gln Gly Leu
                85                  90                  95

Asp Asn Val His Lys Gln Arg Val Ala Glu Val Leu Asn Asp Pro Glu
            100                 105                 110

Asn Met Glu Lys Arg Arg Ser Arg Glu Ser Leu Asn Val Asp Val Val
        115                 120                 125

Lys Tyr Glu Ser Gly Pro Asp Gly Gly Glu Glu Met Arg Lys Met Lys
    130                 135                 140

Leu Gly Leu Val Asn
145

<210> SEQ ID NO 4
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa= R or K
<220> FEATURE:
<221> NAME/KEY: MISC_FEATURE
<222> LOCATION: (5)..(5)
<223> OTHER INFORMATION: Xaa= R or K
<220> FEATURE:
<221> NAME/KEY: MISC_FEATURE
<222> LOCATION: (6)..(6)
<223> OTHER INFORMATION: Xaa= I, L, V, or A
<220> FEATURE:
<221> NAME/KEY: MISC_FEATURE
<222> LOCATION: (7)..(7)
<223> OTHER INFORMATION: Xaa= G or A
<220> FEATURE:
<221> NAME/KEY: MISC_FEATURE
<222> LOCATION: (8)..(9)
<223> OTHER INFORMATION: Xaa= I, L, V, or A
<220> FEATURE:
<221> NAME/KEY: MISC_FEATURE
<222> LOCATION: (10)..(10)

```
<223> OTHER INFORMATION: Xaa= N or Q

<400> SEQUENCE: 4

Met Xaa Xaa Met Xaa Xaa Xaa Xaa Xaa Xaa
1               5                   10

<210> SEQ ID NO 5
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa= R or K
<220> FEATURE:
<221> NAME/KEY: MISC_FEATURE
<222> LOCATION: (5)..(5)
<223> OTHER INFORMATION: Xaa= R or K

<400> SEQUENCE: 5

Met Xaa Xaa Met Xaa Leu Gly Leu Val Asn
1               5                   10

<210> SEQ ID NO 6
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Xaa= I, L, V, or A
<220> FEATURE:
<221> NAME/KEY: MISC_FEATURE
<222> LOCATION: (8)..(9)
<223> OTHER INFORMATION: Xaa= I, L, V, or A

<400> SEQUENCE: 6

Met Arg Lys Met Lys Xaa Gly Xaa Xaa Asn
1               5                   10

<210> SEQ ID NO 7
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa= R or K
<220> FEATURE:
<221> NAME/KEY: MISC_FEATURE
<222> LOCATION: (10)..(10)
<223> OTHER INFORMATION: Xaa= N or Q

<400> SEQUENCE: 7

Met Xaa Xaa Met Lys Leu Gly Leu Val Xaa
1               5                   10

<210> SEQ ID NO 8
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
```

-continued

```
<222> LOCATION: (6)..(6)
<223> OTHER INFORMATION: Xaa= I, L, V, or A
<220> FEATURE:
<221> NAME/KEY: MISC_FEATURE
<222> LOCATION: (8)..(9)
<223> OTHER INFORMATION: Xaa= I, L, V, or A
<220> FEATURE:
<221> NAME/KEY: MISC_FEATURE
<222> LOCATION: (10)..(10)
<223> OTHER INFORMATION: Xaa= N or Q

<400> SEQUENCE: 8

Met Arg Lys Met Lys Xaa Gly Xaa Xaa Xaa
1               5                   10

<210> SEQ ID NO 9
<211> LENGTH: 20
<212> TYPE: DNA
<213> ORGANISM: Artificial sequence
<220> FEATURE:
<223> OTHER INFORMATION: Synthetic knockdown sequence

<400> SEQUENCE: 9
ctcaagagca agtgtataat                                          20

<210> SEQ ID NO 10
<211> LENGTH: 21
<212> TYPE: DNA
<213> ORGANISM: Artificial sequence
<220> FEATURE:
<223> OTHER INFORMATION: Synthetic knockdown sequence

<400> SEQUENCE: 10
aaagatgtac ttgaaggata t                                        21

<210> SEQ ID NO 11
<211> LENGTH: 19
<212> TYPE: DNA
<213> ORGANISM: Artificial sequence
<220> FEATURE:
<223> OTHER INFORMATION: Synthetic

<400> SEQUENCE: 11
tgtatttgtg tctttctaa                                           19

<210> SEQ ID NO 12
<211> LENGTH: 19
<212> TYPE: DNA
<213> ORGANISM: Artificial sequence
<220> FEATURE:
<223> OTHER INFORMATION: Synthetic

<400> SEQUENCE: 12
gcataggaca tgatactaa                                           19

<210> SEQ ID NO 13
<211> LENGTH: 2892
<212> TYPE: DNA
<213> ORGANISM: Homo sapiens

<400> SEQUENCE: 13
atggcggacc tggccgagtg caacatcaaa gtgatgtgtc gcttcagacc tctcaacgag     60
tctgaagtga accgcggcga caagtacatc gccaagtttc agggagaaga cacggtcgtg    120
atcgcgtcca gcctatatgc atttgatcgg gtgttccagt caagcacatc tcaggaacag    180
gtctataatg actgtgcaaa gaagattgtt aaagacgtcc tagagggata taatggaaca    240
```

```
atatttgcat atggacaaac atcctctggg aagacacaca caatggaggg taaacttcat    300
gatccagaag gcatgggaat tattccaaga atagtgcaag atatttttaa ttatatttac    360
tccatggatg aaaatttgga atttcatatt aaggtttcat attttgaaat atatttggat    420
aagataaggg acctgttaga tgtttcaaag accaaccttt cagttcatga agacaaaaac    480
cgagttccct atgtaaaggg gtgcacagag cgttttgtat gtagtccaga tgaagttatg    540
gataccatag atgaaggaaa atccaacaga catgtagcag ttacaaatat gaatgaacat    600
agctctagga gtcacagtat atttcttatt aatgtcaaac aagagaacac acaaacggaa    660
caaaagctga gtggaaaact ttatctggtt gatttagctg gtagtgaaaa ggttagtaaa    720
actggagctg aaggtgctgt gctggatgaa gctaaaaaca tcaacaagtc actttctgct    780
cttggaaatg ttatttctgc tttggctgag ggtagtacat atgttccata tcgagatagt    840
aaaatgacaa gaatccttca agattcatta ggtggcaact gtagaaccac tattgtaatt    900
tgctgctctc catcatcata caatgagtct gaaacaaaat ctacactctt atttggccaa    960
agggccaaaa caattaagaa cacagtttgt gtcaatgtgg agttaactgc agaacagtgg   1020
aaaaagaagt atgaaaaaga aaagaaaaaa aataagatcc tgcggaacac tattcagtgg   1080
cttgaaaatg agctcaacag atggcgtaat ggggagacgg tgcctattga tgaacagttt   1140
gacaaagaga aagccaactt ggaagctttc acagtggata agatattac tcttaccaat    1200 gataaaccag caaccgcaat tggagttata ggaaatttta ctgatgctga agaagaaag    1260 tgtgaagaag aaattgctaa attatacaaa cagcttgatg acaaggatga agaaattaac   1320
cagcaaagtc aactggtaga gaaactgaag acgcaaatgt tggatcagga ggagcttttg   1380
gcatctacca gaagggatca agacaatatg caagctgagc tgaatcgcct tcaagcagaa   1440
aatgatgcct ctaaagaaga agtgaaagaa gttttacagg ccctagaaga acttgctgtc   1500
aattatgatc agaagtctca ggaagttgaa gacaaaacta aggaatatga attgcttagt   1560
gatgaattga atcagaaatc ggcaactta gcgagtatag atgctgagct tcagaaactt   1620
aaggaaatga ccaaccacca gaaaaaacga gcagctgaga tgatggcatc tttactaaaa   1680
gaccttgcag aaataggaat tgctgtggga aataatgatg taaagcagcc tgagggaact   1740
ggcatgatag atgaagagtt cactgttgca agactctaca ttagcaaaat gaagtcagaa   1800
gtaaaaacca tggtgaaacg ttgcaagcag ttagaaagca cacaaactga gagcaacaaa   1860
aaaatggaag aaaatgaaaa ggagttagca gcatgtcagc ttcgtatctc tcaacatgaa   1920
gccaaaatca agtcattgac tgaataccct caaaatgtgg aacaaaagaa aagacagttg   1980
gaggaatctg tcgatgccct cagtgaagaa ctagtccagc ttcgagcaca agagaaagtc   2040
catgaaatgg aaaaggagca cttaaataag gttcagactg caaatgaagt taagcaagct   2100
gttgaacagc agatccagag ccatagagaa actcatcaaa aacagatcag tagtttgaga   2160
gatgaagtag aagcaaaagc aaaacttatt actgatcttc aagaccaaaa ccagaaaatg   2220
atgttagagc aggaacgtct aagagtagaa catgagaagt tgaaagccac agatcaggaa   2280
aagagcagaa aactacatga acttacggtt atgcaagata gacgagaaca agcaagacaa   2340
gacttgaagg gtttggaaga gacagtggca aaagaacttc agactttaca caacctgcgc   2400
aaactctttg ttcaggacct ggctacaaga gttaaaaaga gtgctgagat tgattctgat   2460
gacaccggag gcagcgctgc tcagaagcaa aaaatctcct tcttgaaaaa taatcttgaa   2520
cagctcacta aagtgcacaa acagttggta cgtgataatg cagatctccg ctgtgaactt   2580
```

-continued

| | | | | | |
|---|---|---|---|---|---|
| cctaagttgg | aaaagcgact | tcgagctaca | gctgagagag | tgaaagcttt | ggaatcagca | 2640 |
| ctgaaagaag | ctaaagaaaa | tgcatctcgt | gatcgcaaac | gctatcagca | agaagtagat | 2700 |
| cgcataaagg | aagcagtcag | gtcaaagaat | atggccagaa | gagggcattc | tgcacagatt | 2760 |
| gctaaaccta | ttcgtcccgg | gcaacatcca | gcagcttctc | caactcaccc | aagtgcaatt | 2820 |
| cgtggaggag | gtgcatttgt | tcagaacagc | cagccagtgg | cagtgcgagg | tggaggaggc | 2880 |
| aaacaagtgt | aa | | | | | 2892 |

ANTI-INFLAMMATORY TREATMENT VIA INHIBITION OF ENDOTHELIAL CELL KINESIN LIGHT CHAIN 1, VARIANT 1 (KLC1C)

CROSS REFERENCE TO RELATED APPLICATION

The present application is a continuation of U.S. patent application Ser. No. 16/519,721, filed Jul. 23, 2019, which is a continuation of U.S. patent application Ser. No. 15/401,794, filed Jan. 9, 2017, which claims the priority benefit of U.S. Provisional Patent Application 62/276,503, filed Jan. 8, 2016, which are incorporated by reference in their entireties.

This invention was made with government support under grant numbers F31 HL114374, RO1 HL046849, R37HL064774 awarded by the National Institutes of Health. The government has certain rights in the invention.

FIELD

Provided herein are compositions and methods for the inhibition of endothelial cell kinesin light chain 1, variant 1 (KLC1C) expression and/or activity, and treatment or prevention of inflammation therewith.

BACKGROUND

The inflammatory response is crucial for eliminating foreign microorganisms and healing wounds, but uncontrolled inflammation is responsible for most pathology including diseases such as atherosclerosis and rheumatoid arthritis. A critical step in the inflammatory response is diapedesis, or transendothelial migration (TEM) (ref 1-3; herein incorporated by reference in their entireties). In this step, leukocytes move across the endothelium, into the damaged tissue. This occurs most often at endothelial cell borders (paracellular migration). To reach a site of inflammation in the lumen of epithelial-lined organs, leukocytes have to cross the epithelium in addition to the endothelium in order to get to the site of inflammation (ref. 4; herein incorporated by reference in its entirety).

The lateral border recycling compartment (LBRC) is membrane compartment in endothelial cells that regulates TEM (refs. 5,6; herein incorporated by reference in their entireties). The LBRC comprises interconnected membrane vesicle-like structures that cycle between the parajunctional region and the junctional surface of the endothelium. The LBRC is distinct from typical recycling endosomes, vesiculo-vacuolar organelles, and caveolae (refs. 5,7; herein incorporated by reference in their entireties). Moreover, since it is always connected in some places to the lateral border, it is not totally internalized, and can be thought of as very tortuous invaginations of the lateral border membrane (refs. 5,8-9; herein incorporated by reference in their entireties). Thus, "targeted recycling" is a term used for convenience; membrane fusion is not necessarily involved.

The LBRC contains a subset of membrane proteins, such as platelet endothelial cell adhesion molecule-1 (PECAM), poliovirus receptor (ref 10; herein incorporated by reference in its entirety), CD99, and junctional adhesion molecule-A (ref. 11; herein incorporated by reference in its entirety). At rest, the membrane moves constitutively between the LBRC and the endothelial cell borders with a half time of ~10 min (ref 5; herein incorporated by reference in its entirety). In this constitutive process LBRC membrane recycles evenly along the endothelial borders (refs. 5,6; herein incorporated by reference in its entirety). During TEM, however, membrane from the LBRC is directed to the site at the endothelial cell borders where the leukocyte is transmigrating. This "targeted recycling" facilitates TEM by delivering membrane surface area and specific adhesion/signaling molecules to the migrating leukocyte. Inhibiting targeted recycling of the LBRC blocks leukocyte TEM (ref. 5; herein incorporated by reference in its entirety).

Targeted recycling of the LBRC requires functional microtubules and kinesin molecular motors (ref. 6; herein incorporated by reference in its entirety). Microinjection of endothelial cells with a polyclonal antibody against the conserved motor domain of Drosophila conventional kinesin inhibited targeted recycling and TEM to a similar magnitude as blocking PECAM or depolymerizing microtubules (ref. 6; herein incorporated by reference in its entirety).

SUMMARY

Provided herein are compositions and methods for the inhibition of endothelial cell kinesin light chain 1, variant 1 (KLC1C) expression and/or activity, and treatment or prevention of inflammation therewith.

In some embodiments, provided herein are methods of treating, preventing, or reducing inflammation in a subject comprising administering: (i) a kinesin-1 inhibitor, (ii) a kinesin light chain (KLC) inhibitor, or (iii) a kinesin light chain 1, variant 1 (KLC1C) inhibitor to the subject. In some embodiments, the inhibitor prevents or reduces the expression of kinesin-1, KLC, and/or KLC1C. In some embodiments, the inhibitor binds to and reduces the activity of kinesin-1, KLC, and/or KLC1C. In some embodiments, the inhibitor is an oligonucleotide, peptide, antibody, or small molecule. In some embodiments, administration of the inhibitor inhibits and/or reduces targeted recycling and/or TEM in the subject. In some embodiments, methods further comprise administering a second anti-inflammatory agent (e.g., NSAID, corticosteroid, etc.) to the subject. In some embodiments, the inhibitor is administered systemically or locally. In some embodiments, the inhibitor is administered to endothelial or epithelial cells.

In some embodiments, provided herein are pharmaceutical compositions comprising: (i) a kinesin-1 inhibitor, (ii) a kinesin light chain (KLC) inhibitor, or (iii) a kinesin light chain 1, variant 1 (KLC1C) inhibitor. In some embodiments, the inhibitor is an oligonucleotide, peptide, antibody, or small molecule. In some embodiments, pharmaceutical compositions further comprise one or more additional co-formulated anti-inflammatory agents (e.g., NSAID, corticosteroid, etc.).

In some embodiments, provided herein in the use of (i) a kinesin-1 inhibitor, (ii) a kinesin light chain (KLC) inhibitor, or (iii) a kinesin light chain 1, variant 1 (KLC1C) inhibitor for the treatment of inflammation.

In some embodiments, provided herein are methods of treating, preventing, or reducing inflammation in a subject comprising administering to the subject an agent that inhibits the binding of kinesin light chain 1, variant 1 (KLC1C) to its cargo. In some embodiments, administering said agent inhibits transendothelial migration (TEM) of leukocytes. In some embodiments, administering said agent inhibits targeted recycling of the lateral border recycling compartment (LBRC). In some embodiments, the agent prevents or reduces the expression of KLC1C. In some embodiments, the agent is a nucleic acid. In some embodiments, the agent is an shRNA, siRNA, or antisense oligonucleotide. In some embodiments, the agent inhibits binding of KLC1C to its cargo. In some embodiments, the agent is a peptide, antibody, or small molecule. In some embodiments, the agent is soluble, cell-permeable, and biocompatible. In some embodiments, methods further comprise administering a second anti-inflammatory agent to the subject. In some embodiments, the agent is administered systemically or locally. In some embodiments, the agent is administered to endothelial or epithelial cells. In some embodiments, the agent is a peptide, polypeptide, or peptidomimetic that competes with KLC1C for binding to its cargo. In some embodiments, the agent comprises an amino acid sequence having at least 70% sequence identity to SEQ ID NO: 2. In some embodiments, the agent comprises an amino acid sequence having at least 80% sequence similarity to SEQ ID NO: 2. In some embodiments, the agent comprises an amino acid sequence comprising SEQ ID NO: 2.

In some embodiments, provided herein are pharmaceutical compositions comprising a peptide, polypeptide, or peptidomimetic that competes with KLC1C for binding to its cargo. In some embodiments, the agent comprises an amino acid sequence having at least 70% sequence identity to SEQ ID NO: 2. In some embodiments, the agent comprises an amino acid sequence having at least 80% sequence similarity to SEQ ID NO: 2. In some embodiments, the agent comprises an amino acid sequence comprising SEQ ID NO: 2.

BRIEF DESCRIPTION OF THE DRAWINGS

FIGS. 2A-2B. Sequence of KHC rescue construct (SEQ ID NO: 13). The mutated regions are in bold font and underlined.

DEFINITIONS

Figure 1A:
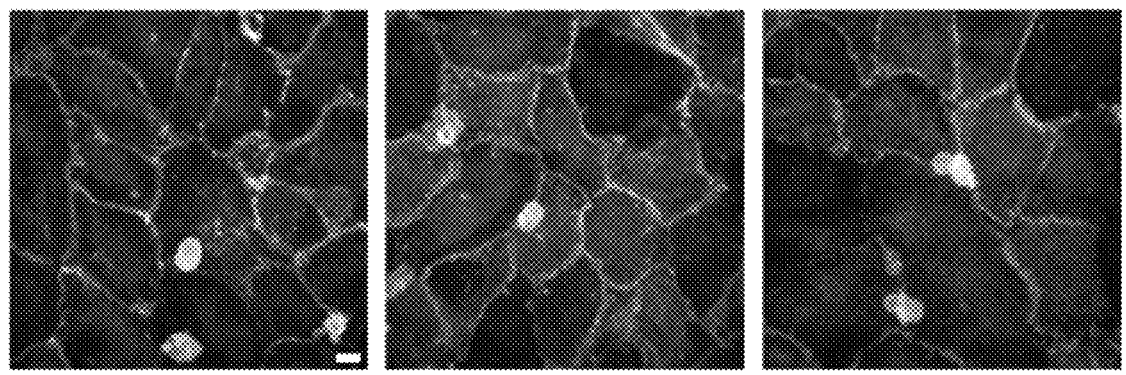
FIGS. 1A-1G. Blocking Kinesin-1 function via microinjection of SUK4 in HUVEC inhibits TEM and targeted recycling. HUVEC were microinjected with SUK4 (Kinesin-1 mAb) or isotype matched mouse IgG control antibody. Antibodies were mixed with a fluorescent-conjugated dextran to label injected cells. Monocytes were allowed to settle on the monolayer and then transmigrate for 7.5 minutes. A) HUVEC monolayers (labeled by PECAM) remained intact following microinjection (microinjected cells) and monocyte TEM. Confocal stacks were imaged and B) the numbers of PBMC that have attached and migrated to EC junctions were counted, and C) TEM was quantified. D) High power images of confocal stacks to show differences in TEM and targeted recycling in SUK4-versus IgG control-microinjected cells. Constitutive recycling occurs evenly but spottily along the junctions; however, targeted recycling enhances LBRC fluorescence at sites of TEM. The monocyte shown is just starting TEM, as seen in the orthogonal projection. Arrowhead indicate site of leukocyte TEM. Dotted lines in the orthogonal projection indicate abluminal surface of endothelial cells. E) LBRC enrichment was measured around leukocytes at endothelial junctions. F) Targeted recycling was significantly diminished after microinjection of SUK4 mAb against Kinesin-1. G) TEM was significantly lower in SUK4-injected cells compared to that of cells injected with K2.4 (anti-Kinesin-2). Scale bar=10 µm.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular embodiments, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a peptide" is a reference to one or more peptides and equivalents thereof known to those skilled in the art, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the terms "kinesin-1 inhibitor," "KLC inhibitor," "KLC1C inhibitor," or linguistic variants thereof (e.g., "inhibitor of KLC1C," "KLC1C inhibiting agent," etc.) refer to an agent that attenuates the expression of kinesin-1, KLC, or KLC1C, respectively (e.g., interferes with gene expression), including suppression of transcription or translation; and/or an agent that directly inhibits kinesin-1, KLC, or KLC1C activity (e.g., cargo binding), for example by binding to kinesin-1, KLC, or KLC1C, respectively.

As used herein, the term "subject" broadly refers to any animal, including but not limited to, human and non-human animals (e.g., dogs, cats, cows, horses, sheep, poultry, fish, crustaceans, etc.). As used herein, the term "patient" typically refers to a human subject that is being treated for a disease or condition or prophylactically.

The term "amino acid" refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids include, but are not limited to, azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), N-alkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("OctG"), ornithine ("Orn"), pentylglycine ("pG" or "PGly"), pipecolic acid, thioproline ("ThioP" or "tPro"), homoLysine ("hLys"), and homoArginine ("hArg").

The term "amino acid analog" refers to a natural or unnatural amino acid where one or more of the C-terminal carboxy group, the N-terminal amino group and side-chain functional group has been chemically blocked, reversibly or irreversibly, or otherwise modified to another functional group. For example, aspartic acid-(beta-methyl ester) is an amino acid analog of aspartic acid; N-ethylglycine is an amino acid analog of glycine; or alanine carboxamide is an amino acid analog of alanine. Other amino acid analogs include methionine sulfoxide, methionine sulfone, S-(carboxymethyl)-cysteine, S-(carboxymethyl)-cysteine sulfoxide and S-(carboxymethyl)-cysteine sulfone.

As used herein, the term "peptide" refers a short polymer of amino acids linked together by peptide bonds. In contrast to other amino acid polymers (e.g., proteins, polypeptides, etc.), peptides are of about 50 amino acids or less in length. A peptide may comprise natural amino acids, non-natural amino acids, amino acid analogs, and/or modified amino acids. A peptide may be a subsequence of naturally occurring protein or a non-natural (synthetic) sequence.

As used herein, the term "mutant peptide" refers to a peptide having a distinct amino acid sequence from the most common variant occurring in nature, referred to as the "wild-type" sequence. A mutant peptide may be a subsequence of a mutant protein or polypeptide (e.g., a subsequence of a naturally-occurring protein that is not the most common sequence in nature) or may be a peptide that is not a subsequence of a naturally occurring protein or polypeptide. For example, a "mutant C-terminal KLC1C peptide" may be a subsequence of a naturally-occurring, non-wild-type C-terminal KLC1C peptide, or may be distinct sequence not found in naturally-occurring KLC1C polypeptides.

As used herein, the term "artificial peptide" or "artificial polypeptide" refers to a peptide or polypeptide having a distinct amino acid sequence from those found in natural peptides and/or proteins. An artificial protein is not a subsequence of a naturally occurring protein, either the wild-type (i.e., most abundant) or mutant versions thereof. For example, an artificial KLC1C c-terminal peptide is not a subsequence of naturally occurring KLC1C. An artificial peptide or polypeptide may be produced or synthesized by any suitable method (e.g., recombinant expression, chemical synthesis, enzymatic synthesis, etc.).

The terms "peptide mimetic" or "peptidomimetic" refer to a peptide-like molecule that emulates a sequence derived from a protein or peptide. A peptide mimetic or peptidomimetic may contain amino acids and/or non-amino acid components. Examples of peptidomimitecs include chemically modified peptides, peptoids (side chains are appended to the nitrogen atom of the peptide backbone, rather than to the α-carbons), β-peptides (amino group bonded to the β carbon rather than the α carbon), etc.

As used herein, a "conservative" amino acid substitution refers to the substitution of an amino acid in a peptide or polypeptide with another amino acid having similar chemical properties, such as size or charge. For purposes of the present disclosure, each of the following eight groups contains amino acids that are conservative substitutions for one another:

1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M), and Valine (V);
6) Phenylalanine (F), Tyrosine (Y), and Tryptophan (W);
7) Serine (S) and Threonine (T); and
8) Cysteine (C) and Methionine (M).

Naturally occurring residues may be divided into classes based on common side chain properties, for example: polar positive (histidine (H), lysine (K), and arginine (R)); polar negative (aspartic acid (D), glutamic acid (E)); polar neutral (serine (S), threonine (T), asparagine (N), glutamine (Q)); non-polar aliphatic (alanine (A), valine (V), leucine (L), isoleucine (I), methionine (M)); non-polar aromatic (phenylalanine (F), tyrosine (Y), tryptophan (W)); proline and glycine; and cysteine. As used herein, a "semi-conservative" amino acid substitution refers to the substitution of an amino acid in a peptide or polypeptide with another amino acid within the same class.

In some embodiments, unless otherwise specified, a conservative or semi-conservative amino acid substitution may also encompass non-naturally occurring amino acid residues that have similar chemical properties to the natural residue. These non-natural residues are typically incorporated by chemical peptide synthesis rather than by synthesis in biological systems. These include, but are not limited to, peptidomimetics and other reversed or inverted forms of amino acid moieties. Embodiments herein may, in some embodiments, be limited to natural amino acids, non-natural amino acids, and/or amino acid analogs.

Non-conservative substitutions may involve the exchange of a member of one class for a member from another class.

As used herein, the term "sequence identity" refers to the degree to which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) differ only by conservative and/or semi-conservative amino acid substitutions. The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

As used herein, the term "antibody" refers to a whole antibody molecule or a fragment thereof (e.g., fragments such as Fab, Fab', and F(ab')2), unless otherwise specified (e.g., "full-length antibody," "antibody fragment," etc.). An antibody may be a polyclonal or monoclonal antibody, a chimeric antibody, a humanized antibody, a human antibody, etc.

A native antibody typically has a tetrameric structure. A tetramer typically comprises two identical pairs of polypeptide chains, each pair having one light chain (in certain embodiments, about 25 kDa) and one heavy chain (in certain embodiments, about 50-70 kDa). In a native antibody, a heavy chain comprises a variable region, VH, and three constant regions, CH1, CH2, and CH3. The VH domain is at the amino-terminus of the heavy chain, and the CH3 domain is at the carboxy-terminus. In a native antibody, a light chain comprises a variable region, VL, and a constant region, CL. The variable region of the light chain is at the amino-terminus of the light chain. In a native antibody, the variable regions of each light/heavy chain pair typically form the antigen binding site. The constant regions are typically responsible for effector function. In a native antibody, the variable regions typically exhibit the same general structure in which relatively conserved framework regions (FRs) are joined by three hypervariable regions, also called complementarity determining regions (CDRs). The CDRs from the two chains of each pair typically are aligned by the framework regions, which may enable binding to a specific epitope. From N-terminus to C-terminus, both light and heavy chain variable regions typically comprise the domains FR1, CDR1, FR2, CDR2, FR3, CDR3 and FR4. The CDRs on the heavy chain are referred to as H1, H2, and H3, while the CDRs on the light chain are referred to as L1, L2, and L3. Typically, CDR3 is the greatest source of molecular diversity within the antigen-binding site. H3, for example, in certain instances, can be as short as two amino acid residues or greater than 26. The assignment of amino acids to each domain is typically in accordance with the definitions of Kabat et al. (1991) Sequences of Proteins of Immunological Interest (National Institutes of Health, Publication No. 91-3242, vols. 1-3, Bethesda, Md.); Chothia, C., and Lesk, A. M. (1987) J. Mol. Biol. 196:901-917; or Chothia, C. et al. Nature 342:878-883 (1989). In the present application, the term "CDR" refers to a CDR from either the light or heavy chain, unless otherwise specified.

As used herein, the term "heavy chain" refers to a polypeptide comprising sufficient heavy chain variable region sequence to confer antigen specificity either alone or in combination with a light chain.

As used herein, the term "light chain" refers to a polypeptide comprising sufficient light chain variable region sequence to confer antigen specificity either alone or in combination with a heavy chain.

As used herein, when an antibody or other entity "specifically recognizes" or "specifically binds" an antigen or epitope, it preferentially recognizes the antigen in a complex mixture of proteins and/or macromolecules, and binds the antigen or epitope with affinity which is substantially higher than to other entities not displaying the antigen or epitope. In this regard, "affinity which is substantially higher" means affinity that is high enough to enable detection of an antigen or epitope which is distinguished from entities using a desired assay or measurement apparatus. Typically, it means binding affinity having a binding constant (Ka) of at least $10^7$ M$^{-1}$ (e.g., >$10^7$ M$^{-1}$, >$10^8$ M$^{-1}$, >$10^9$ M$^{-1}$, >$10^{10}$ M$^{-1}$, >$10^{11}$ M-1, >$10^{12}$ M$^{-1}$, >$10^{13}$ M$^{-1}$, etc.). In certain such embodiments, an antibody is capable of binding different antigens so long as the different antigens comprise that particular epitope. In certain instances, for example, homologous proteins from different species may comprise the same epitope.

As used herein, the term "monoclonal antibody" refers to an antibody which is a member of a substantially homogeneous population of antibodies that specifically bind to the same epitope. In certain embodiments, a monoclonal antibody is secreted by a hybridoma. In certain such embodiments, a hybridoma is produced according to certain methods known to those skilled in the art. See, e.g., Kohler and Milstein (1975) Nature 256: 495-499; herein incorporated by reference in its entirety. In certain embodiments, a monoclonal antibody is produced using recombinant DNA methods (see, e.g., U.S. Pat. No. 4,816,567). In certain embodiments, a monoclonal antibody refers to an antibody fragment isolated from a phage display library. See, e.g., Clackson et al. (1991) Nature 352: 624-628; and Marks et al. (1991) J. Mol. Biol. 222: 581-597; herein incorporated by reference in their entireties. The modifying word "monoclonal" indicates properties of antibodies obtained from a substantially-homogeneous population of antibodies, and does not limit a method of producing antibodies to a specific method. For various other monoclonal antibody production techniques, see, e.g., Harlow and Lane (1988) Antibodies: A Laboratory Manual (Cold Spring Harbor Laboratory, Cold Spring Harbor, N.Y.); herein incorporated by reference in its entirety.

As used herein, the term "antibody fragment" refers to a portion of a full-length antibody, including at least a portion antigen binding region or a variable region. Antibody fragments include, but are not limited to, Fab, Fab', F(ab')2, Fv, scFv, Fd, diabodies, and other antibody fragments that retain at least a portion of the variable region of an intact antibody. See, e.g., Hudson et al. (2003) Nat. Med. 9:129-134; herein incorporated by reference in its entirety. In certain embodiments, antibody fragments are produced by enzymatic or chemical cleavage of intact antibodies (e.g., papain digestion and pepsin digestion of antibody). produced by recombinant DNA techniques, or chemical polypeptide synthesis.

For example, a "Fab" fragment comprises one light chain and the CH1 and variable region of one heavy chain. The heavy chain of a Fab molecule cannot form a disulfide bond with another heavy chain molecule. A "Fab'" fragment comprises one light chain and one heavy chain that comprises additional constant region, extending between the CH1 and CH2 domains. An interchain disulfide bond can be formed between two heavy chains of a Fab' fragment to form a "F(ab')2" molecule.

An "Fv" fragment comprises the variable regions from both the heavy and light chains, but lacks the constant regions. A single-chain Fv (scFv) fragment comprises heavy and light chain variable regions connected by a flexible linker to form a single polypeptide chain with an antigen-binding region. Exemplary single chain antibodies are discussed in detail in WO 88/01649 and U.S. Pat. Nos. 4,946,778 and 5,260,203; herein incorporated by reference in their entireties. In certain instances, a single variable region (e.g., a heavy chain variable region or a light chain variable region) may have the ability to recognize and bind antigen.

Other antibody fragments will be understood by skilled artisans.

As used herein, the term "chimeric antibody" refers to an antibody made up of components from at least two different sources. In certain embodiments, a chimeric antibody comprises a portion of an antibody derived from a first species fused to another molecule, e.g., a portion of an antibody derived from a second species. In certain such embodiments, a chimeric antibody comprises a portion of an antibody derived from a non-human animal fused to a portion of an antibody derived from a human. In certain such embodiments, a chimeric antibody comprises all or a portion of a variable region of an antibody derived from a non-human animal fused to a constant region of an antibody derived from a human.

A "humanized" antibody refers to a non-human antibody that has been modified so that it more closely matches (in amino acid sequence) a human antibody. A humanized antibody is thus a type of chimeric antibody. In certain embodiments, amino acid residues outside of the antigen binding residues of the variable region of the non-human antibody are modified. In certain embodiments, a humanized antibody is constructed by replacing all or a portion of a complementarity determining region (CDR) of a human antibody with all or a portion of a CDR from another antibody, such as a non-human antibody, having the desired antigen binding specificity. In certain embodiments, a humanized antibody comprises variable regions in which all or substantially all of the CDRs correspond to CDRs of a non-human antibody and all or substantially all of the framework regions (FRs) correspond to FRs of a human antibody. In certain such embodiments, a humanized antibody further comprises a constant region (Fc) of a human antibody.

The term "human antibody" refers to a monoclonal antibody that contains human antibody sequences and does not contain antibody sequences from a non-human animal. In certain embodiments, a human antibody may contain synthetic sequences not found in native antibodies. The term is not limited by the manner in which the antibodies are made. For example, in various embodiments, a human antibody may be made in a transgenic mouse, by phage display, by human B-lymphocytes, or by recombinant methods.

As used herein, the term "natural antibody" refers to an antibody in which the heavy and light chains of the antibody have been made and paired by the immune system of a multicellular organism. For example, the antibodies produced by the antibody-producing cells isolated from a first animal immunized with an antigen are natural antibodies. Natural antibodies contain naturally-paired heavy and light chains. The term "natural human antibody" refers to an antibody in which the heavy and light chains of the antibody have been made and paired by the immune system of a human subject.

Native human light chains are typically classified as kappa and lambda light chains. Native human heavy chains are typically classified as mu, delta, gamma, alpha, or epsilon, and define the antibody's isotype as IgM, IgD, IgG, IgA, and IgE, respectively. IgG has subclasses, including, but not limited to, IgG1, IgG2, IgG3, and IgG4. IgM has subclasses including, but not limited to, IgM1 and IgM2. IgA has subclasses including, but not limited to, IgA1 and IgA2. Within native human light and heavy chains, the variable and constant regions are typically joined by a "J" region of about 12 or more amino acids, with the heavy chain also including a "D" region of about 10 more amino acids. See, e.g., Fundamental Immunology (1989) Ch. 7 (Paul, W., ed., 2nd ed. Raven Press, N.Y.); herein incorporated by reference in its entirety.

The term "neutralizing antibody" or "antibody that neutralizes" refers to an antibody that reduces at least one activity of a polypeptide comprising the epitope to which the antibody specifically binds. In certain embodiments, a neutralizing antibody reduces an activity in vitro and/or in vivo.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

The term "siRNAs" refers to short interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

As used herein, the terms "administration" and "administering" refer to the act of giving a drug, prodrug, or other agent, or therapeutic to a subject or in vivo, in vitro, or ex vivo cells, tissues, and organs. Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

The term "treatment" encompasses both therapeutic and prophylactic/preventative measures unless otherwise indicated. Those in need of treatment include, but are not limited to, individuals already having a particular condition (e.g., caused by or resulting in inflammation) as well as individuals who are at risk of acquiring a particular condition or disorder (e.g., those needing prophylactic/preventative measures). The term "treating" refers to administering an agent to a subject for therapeutic and/or prophylactic/preventative purposes.

A "therapeutic agent" refers to an agent that may be administered in vivo to bring about a therapeutic and/or prophylactic/preventative effect.

As used herein, the terms "co-administration" and "co-administering" refer to the administration of at least two agent(s) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

DETAILED DESCRIPTION

Provided herein are compositions and methods for the inhibition of endothelial cell kinesin light chain 1, variant 1 (KLC1C) expression and/or activity, and treatment or prevention of inflammation therewith.

Experiments conducted during development of embodiments herein demonstrate that endothelial cell Kinesin-1 is the kinesin heavy chain involved in transporting the LBRC to the site of TEM (targeted recycling) and thereby supporting TEM. Inhibiting expression or activity of Kinesin-1 (e.g., knocking down Kinesin-1 in endothelial cells, microinjecting a function-blocking monoclonal antibody specific for Kinesin-1 into endothelial cells, etc.) blocked targeted recycling and TEM. Further, KLC1, and more specifically isoform variant 1 of KLC1 (KLC1C), is critical for targeted recycling of the LBRC and TEM. Since kinesin light chains mediate the binding of cargo to kinesin heavy chains, this indicates that KLC1C is responsible for the binding of the LBRC to Kinesin-1 during targeted recycling and TEM; although embodiments herein are not limited to any particular mechanism of action and an understanding of the mechanism of action is not necessary to practice embodiments herein.

To determine which kinesin was responsible for moving the LBRC during targeted recycling, experiments were conducted to determine which kinesin genes were expressed in endothelial cells. Using RT-PCR, expression of 23 of the 45 known kinesin genes was detected. After eliminating the mitotic kinesins (which function during cytokinesis, chromosome segregation, and microtubule destabilization) and minus-end motors (since paracellular migration would require plus-end movement to the site of TEM at endothelial junctions) from consideration, 13 candidates remained. Kinesin-1 was selected for initial analysis because of the availability of a function-blocking monoclonal antibody (SUK4) for kinesin-1. HUVEC express KIF5B and KIF5C (ref. 6; herein incorporated by reference in its entirety); SUK4 recognizes both gene products (ref 28; herein incorporated by reference in its entirety).

Experiments conducted during development of embodiments herein demonstrate that targeted recycling and TEM are reduced by 75% to over 95% by interfering with Kinesin-1 or KLC1C, demonstrating that these proteins are critical for efficient targeted recycling and TEM. Since KIF5B is ubiquitously expressed, and knocking it down has such a large effect on targeted recycling of the LBRC and TEM, the effect of knocking down other kinesin heavy chains or even other Kinesin-1 isoforms in the presence of endogenous KIF5B is minimal. Ofr example, microinjecting K2.4 mAb against Kinesin-2 in HUVEC did not affect TEM levels.

The TEM assay is an endpoint assay in which leukocytes are observed after 1 hour of allowing them to migrate across endothelial cell junctions. This demonstrates that knockdown of Kinesin-1 or KLC1, variant 1 does not merely slow down TEM; it inhibits it. The targeted recycling assay catches leukocytes in the act of transmigration (~8 minutes of migration). Catching leukocytes during migration provides the opportunity to observe enrichment of the LBRC around migrating leukocytes. These assays are performed and completed within a few hours of microinjection, so the effect of blocking Kinesin-1 function on other physiologic processes is minimal. Furthermore, control cells are injected with an equal volume and concentration of control rabbit IgG. Notably, interference with Kinesin-1 or KLC1C had no effect on adhesion of monocytes to the endothelial monolayers or migration of monocytes to the endothelial cell borders (FIG. 1, 3, 5). It was specific for inhibiting targeted recycling and TEM, as was depolymerization of microtubules by chemical means and microinjection of HD polyclonal antibody. Moreover, interfering with kinesin function has no effect on constitutive recycling of the LBRC; kinesin-1 and KLC1C disruption only affects targeted recycling of the LBRC to the site of TEM.

Kinesin (e.g., kinesin-1) is a tetrameric molecule composed of two heavy chains and two light chains, which transports various cargos along microtubules toward their plus ends. The heavy chains typically provide the motor activity, while the light chains bind to various cargos. Some cargoes may actually bind directly to the kinesin heavy chain, such as milton, which competes with light chains for binding to the heavy chain (refs 16-17; herein incorporated by reference in their entireties). Kinesin light chains are composed of an α-helical coiled-coil heptad repeat domain that binds to the kinesin heavy chain, six imperfect tetratricopeptide repeats that mediate cargo-binding (refs. 39-42; herein incorporated by reference in their entireties) and a variable C-terminal domain (ref. 38; herein incorporated by reference in its entirety). Known kinesin light chains include kinesin light chain 1 (KLC1), kinesin light chain 2 (KLC2), kinesin light chain 3 (KLC3), kinesin light chain 4 (KLC4). Kinesin light chain 1 (KLC1) is a protein that in humans is encoded by the KLC1 gene. Due to alternative splicing in this C-terminal domain, different KLC1 variants have been proposed to mediate binding to specific cargoes such as vimentin, mitochondria, and Golgi membranes (refs. 37,43-45; herein incorporated by reference in their entireties). Specifically, human KLC1 isoform variant E has been suggested to play a role in intracellular trafficking in amyloid-β accumulation (refs. 46-48; herein incorporated by reference in their entireties). Amyloid-β accumulation is typical of Alzheimer's disease, and knocking down KLC1E in neuroblastoma cells decreased the levels of amyloid-β. Conversely, overexpression of this variant increased amyloid-β levels.

Experiments conducted during development of embodiments herein demonstrate that KLC1 isoform variant 1 (KLC1C) is a key factor in targeted recycling and TEM. Kinesin heavy chains process along microtubules carrying bound cargo in the direction of the "plus" end. Kinesin light chains bind a restricted range of cargoes and tether them to kinesin heavy chains by binding to the carboxy terminal of the heavy chains. Data demonstrate that KLC1C is the link between Kinesin-1 and the LBRC cargo during targeted recycling.

In some embodiments, various KLC1 variants (isoforms) are of a predominantly identical sequence (SEQ ID NO: 1). In some embodiments, a KLC1 variant comprises a predominant region with at least 70% sequence identity to SEQ ID NO: 1 (e.g., 70%, 75%, 80%, 85%, 90%, 95%, or more, or ranges therebetween (e.g., 90% or more, 70-90%, etc.)). In some embodiments, KLC1 variants (isoforms) differ at the C-terminus, thereby conferring cargo specificity. In some embodiments, a KLC1 variant comprises the predominant KLC1 sequence (SEQ ID NO: 1) and a C-terminal cargo-specificity peptide (e.g., SEQ ID NO: 2). For example, KLC1 variant 1 (KLC1C) comprises the predominant KLC1 sequence (SEQ ID NO: 1) and a C-terminal cargo-specificity peptide of MRKMKLGLVN (SEQ ID NO: 2). In some embodiments, KLC1C comprises SEQ ID NO: 3. In some embodiments, KLC1C comprises a portion with at least 70% sequence identity to SEQ ID NO: 1 (e.g., 70%, 75%, 80%, 85%, 90%, 95%, 99%, or more, or ranges therebetween (e.g., 80% or more, 90% or more, 70-90%, etc.)). In some embodiments, KLC1C comprises a portion at least 70% sequence identity to SEQ ID NO: 2 (e.g., 70%, 80%, 90%, or more, or ranges therebetween (e.g., 80% or more, 90% or more, 70-90%, etc.)). In some embodiments, KLC1C comprises at least 70% sequence identity to SEQ ID NO: 3 (e.g., 70%, 75%, 80%, 85%, 90%, 95%, 99%, or more, or ranges therebetween (e.g., 80% or more, 90% or more, 70-90%, etc.)). In some embodiments, KLC1C comprises a portion with at least 70% sequence similarity to SEQ ID NO: 1 (e.g., 70%, 75%, 80%, 85%, 90%, 95%, 99%, or more, or ranges therebetween (e.g., 80% or more, 90% or more, 70-90%, etc.)). In some embodiments, KLC1C comprises a portion at least 70% sequence similarity to SEQ ID NO: 2 (e.g., 70%, 80%, 90%, or more, or ranges therebetween (e.g., 80% or more, 90% or more, 70-90%, etc.)). In some embodiments, KLC1C comprises at least 70% sequence similarity to SEQ ID NO: 3 (e.g., 70%, 75%, 80%, 85%, 90%, 95%, 99%, or more, or ranges therebetween (e.g., 80% or more, 90% or more, 70-90%, etc.)).

Experiments conducted during development of embodiments herein demonstrate that the KLC1C variant is a key factor in targeted recycling of the LBRC and transendothelial migration (TEM). Kinesin-1 complexes comprising this light chain variant (KLC1C) are responsible for migration of white blood cells into sites of inflammation. In particular, the C-terminal peptide (SEQ ID NO: 2) of the KLC1C polypeptide (SEQ ID NO: 3) is responsible for the cargo specificity, and the role of KLC1C in TEM, targeted recycling of the LBRC, and/or migration of white blood cells into sites of inflammation.

Accordingly, some embodiments herein relate to targeting of KLC1C and/or its C-terminal peptide region (MRKMKLGLVN (SEQ ID NO: 2)) to inhibit TEM and targeted recycling of the LBRC and to prevent/reduce migration of white blood cells into sites of inflammation. In some embodiments, KLC1C expression is inhibited (e.g., siRNA, shRNA, etc.). In some embodiments, KLC1C binding to its cargo is inhibited (e.g., a small molecule, peptide, antibody, etc.). In some embodiments, a peptide that mimics the C-terminal peptide of KLC1C (e.g., comprising SEQ ID NO: 2, comprising at least 70% sequence identity/similarity to SEQ ID NO: 2) is provided. In some embodiments, a synthetic KLC1C C-terminal peptide is provided to compete with endogenous KLC1C for cargo binding.

In some embodiments, compositions and methods described herein that specifically target KLC1C for the inhibition of TEM and targeted recycling of the LBRC and to prevent/reduce migration of white blood cells into sites of inflammation. Other kinesins, kinesin-1 proteins, kinesin-1 light chain polypeptides, etc. are not targeted, are not affected, or are affected to a significantly lesser degree that KLC1C (e.g., <50%, <25%, <10%, <5%, <1%, <0.1%, <0.01%, <0.001%, or less).

In some embodiments, provided herein are KLC1C C-terminal peptide molecules that comprise at least 70% sequence identity (e.g., 3 or fewer substitutions) with MRKMKLGLVN (SEQ ID NO: 2). In some embodiments, provided herein are peptide molecules that comprise at least 70% (e.g., 70%, 80%, 90%, 100%) sequence similarity (e.g., 3 or fewer non-conservative and/or semi-conservative substitutions) with MRKMKLGLVN (SEQ ID NO: 2). In some embodiments, the KLC1C C-terminal peptide is soluble. In some embodiments, the KLC1C C-terminal peptide is cell permeable. In some embodiments, the KLC1C C-terminal peptide is cell bioactive. In some embodiments, the In some embodiments, the KLC1C C-terminal peptide is cell permeable, enters endothelial cells, inhibits targeted recycling of the lateral border recycling compartment (LBRC) block transendothelial migration of leukocytes, and reduces/inhibits inflammation. In some embodiments, a C-terminal KLC1C peptide is conjugated to one or more functional moieties to impart desirable functionalities (e.g., solubility, bioavailability, cell-permeability) to the peptide. In some embodiments, a peptide/polypeptide functional moiety is conjugated to a C-terminal KLC1C peptide. In some embodiments, the C-terminal KLC1C peptide is conjugated to a cell-penetrating peptide (e.g., trans-activating transcriptional activator (TAT), antennapedia peptide, etc.).

In some embodiments, a KLC1C C-terminal peptide comprises:

```
                                            (SEQ ID NO: 4)
M(R/K)(R/K)M(R/K)(I/L/V/A)(G/A)(I/L/V/A)(I/L/V/A)
(N/Q);

(SEQ ID NO: 5)
M(R/K)(R/K)M(R/K)LGLVN;

(SEQ ID NO: 6)
MRKMK(I/L/V/A)G(I/L/V/A)(I/L/V/A)N;

(SEQ ID NO: 7)
M(R/K)(R/K)MKLGLV(N/Q);

(SEQ ID NO: 8)
MRKMK(I/L/V/A)G(I/L/V/A)(I/L/V/A)(N/Q);
``` or petidomimetcis thereof.

Some embodiments herein broadly relate to methods for the treatment or prevention of inflammation in a subject (e.g., a subject having or at risk of a disease or condition for which an inflammatory state is an underlying cause, a subject having or at risk of a disease or condition in which inflammation is a symptom) comprising administering to the subject (or providing the subject with) an agent capable of inhibiting (e.g., attenuating the expression or activity of) kinesin-1, kinesin light chain (KLC), or kinesin light chain 1, variant 1 (KLC1C). In some embodiments, the inhibition of kinesin-1, KLC, or KLC1C reduces (e.g., inhibits) targeted recycling, TEM, and/or inflammation. In some embodiments, kinesin-1, KLC, or KLC1C inhibitor is selected from: (i) an oligonucleotide capable of attenuating the expression of kinesin-1, KLC, or KLC1C (e.g., small interfering RNA (siRNA), small hairpin RNA (shRNA), micro RNA (miRNA), a ribozyme, an antisense oligonucleotide, etc.); (ii) an anti-kinesin-1, anti-KLC, or anti-KLC1C antibody (or antibody fragment), peptide, or polypeptide capable of binding to kinesin-1, KLC, or KLC1C and inhibiting its activity; and a potent small molecule inhibitor of the activity of kinesin-1, KLC, or KLC1C.

In some embodiments, provided herein are pharmaceutical compositions comprising inhibitors of kinesin-1, KLC, and/or KLC1C (e.g., inhibitors of expression and/or activity). In some embodiments, provided herein are pharmaceutical compositions comprising inhibitors of KLC1C expression. In some embodiments, provided herein are pharmaceutical compositions comprising inhibitors of KLC1C cargo binding (e.g., small molecules, peptides, antibodies, etc.). In some embodiments, provided herein are pharmaceutical compositions comprising competitors of KLC1C cargo binding (e.g., synthetic C-terminal KLC1C peptides). Such pharmaceutical compositions comprise a therapeutically effective amount of the active agent and a pharmaceutically acceptable carrier. In some embodiments, the term "pharmaceutically acceptable" means approved by a regulatory agency of the Federal or a state government or listed in the U.S. Pharmacopeia or other generally recognized pharmacopeia for use in animals and more particularly in humans.

In some embodiments, provided herein are bioactive peptide molecules that inhibit KLC1C activity (e.g., inhibit the binding of KLC1C to its cargo). In some embodiments, a peptide inhibitor of KLC1C is provided. In some embodiments, the inhibitor binds to KLC1C (e.g., the C-terminal portion of KLC1C (e.g., SEQ ID NO: 2)) and prevents KLC1C from binding its cargo. In some embodiments, the inhibitor peptide is cell permeable. In some embodiments, the inhibitor peptide enters endothelial cells, binding of KLC1C to its cargo, inhibits targeted recycling of the lateral border recycling compartment (LBRC) block transendothelial migration of leukocytes, and reduces/inhibits inflammation. In some embodiments, an inhibitor peptide is conjugated to one or more functional moieties to impart desirable functionalities (e.g., solubility, bioavailability, cell-permeability) to the peptide. In some embodiments, a peptide/polypeptide functional moiety is conjugated to an inhibitor peptide. In some embodiments, the an inhibitor peptide is conjugated to a cell-penetrating peptide (e.g., trans-activating transcriptional activator (TAT), antennapedia peptide, etc.).

In some embodiments the technology provides antibodies or antibody fragments for inhibiting the binding activity of KLC1C to its cargo. In some embodiments, an antibody or antibody fragment recognizes the C-terminal region of KLC1C (e.g., SEQ ID NO: 2). In some embodiments, an antibody or antibody fragment recognizes an amino acid sequence comprising SEQ ID NO: 2. In some embodiments, an antibody or antibody fragment recognizes an amino acid sequence that is a portion of SEQ ID NO: 2. In some embodiments, an antibody or antibody fragment is specific for KLC1C and does not bind other kinesins or kinesin light chains. In some embodiments, an antibody is a neutralizing antibody. In some embodiments, KLC1C cannot bind its cargo when the antibody is bound.

In some embodiments, the antibody is a monoclonal antibody and in some embodiments the antibody is a polyclonal antibody. In some embodiments, the antibody is, for example, a human, humanized, or chimeric antibody. Monoclonal antibodies against target antigens are produced by a variety of techniques including conventional monoclonal antibody methodologies such as the somatic cell hybridization techniques of Köhler and Milstein (Nature, 256:495 (1975)). Although in some embodiments, somatic cell hybridization procedures are preferred, other techniques for producing monoclonal antibodies are contemplated as well (e.g., viral or oncogenic transformation of B lymphocytes).

In some embodiments the technology provides small molecule agents for inhibiting the binding activity of KLC1C to its cargo. In some embodiments, the small molecule agent binds to KLC1C (e.g., the c-terminus of KLC1C) and prevents KLC1C from binding its cargo (e.g., sterically, by inducing a conformational change, etc.). In some embodiments, the small molecule agent binds to the cargo of KLC1C and prevent sKLC1C (e.g., the c-terminus of KLC1C) from binding its cargo (e.g., sterically, by inducing a conformational change, etc.). In some embodiments, a small molecule agent is soluble, cell permeable, biocompatible, etc.

In some embodiments, compositions and methods are provided to inhibit the expression of KLC1C. In some embodiments, a nucleic acid is used to modulate (e.g., inhibit) expression of KLC1C.

In some embodiments a small interfering RNA (siRNA) is designed to target and degrade a nucleic acid encoding KLC1C. siRNAs are double-stranded RNA molecules of 20-25 nucleotides in length. While not limited in their features, typically an siRNA is 21 nucleotides long and has 2-nt 3' overhangs on both ends. Each strand has a 5' phosphate group and a 3' hydroxyl group. In vivo, this structure is the result of processing by Dicer, an enzyme that converts either long dsRNAs or small hairpin RNAs (shRNAs) into siRNAs. However, siRNAs can also be synthesized and exogenously introduced into cells to bring about the specific knockdown of a gene of interest. Essentially any gene of which the sequence is known can be targeted based on sequence complementarity with an appropriately tailored siRNA. For example, those of ordinary skill in the art can synthesize an siRNA (see, e.g., Elbashir, et al., Nature 411:494 (2001); Elbashir, et al. Genes Dev 15:188 (2001); Tuschl T, et al., Genes Dev 13:3191 (1999)).

In some embodiments, RNAi is utilized to inhibit KLC1C. RNAi represents an evolutionarily conserved cellular defense for controlling the expression of foreign genes in most eukaryotes, including humans. RNAi is typically triggered by double-stranded RNA (dsRNA) and causes sequence-specific degradation of single-stranded target RNAs (e.g., an mRNA). The mediators of mRNA degradation are small interfering RNAs (siRNAs), which are normally produced from long dsRNA by enzymatic cleavage in the cell. siRNAs are generally approximately twenty-one nucleotides in length (e.g. 21-23 nucleotides in length) and have a base-paired structure characterized by two-nucleotide 3' overhangs. Following the introduction of a small RNA, or RNAi, into the cell, it is believed the sequence is delivered to an enzyme complex called RISC (RNA-induced silencing complex). RISC recognizes the target and cleaves it with an endonuclease. It is noted that if larger RNA sequences are delivered to a cell, an RNase III enzyme (e.g., Dicer) converts the longer dsRNA into 21-23 nt double-stranded siRNA fragments. In some embodiments, RNAi oligonucleotides are designed to target KLC1C.

In other embodiments, shRNA techniques (See e.g., 20080025958, herein incorporated by reference in its entirety) are utilized to modulate (e.g., inhibit) expression of KLC1C. A small hairpin RNA or short hairpin RNA (shRNA) is a sequence of RNA that makes a tight hairpin turn that can be used to silence gene expression via RNA interference. shRNA uses a vector introduced into cells and utilizes the U6 promoter to ensure that the shRNA is always expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs that match the siRNA that is bound to it. shRNA is transcribed by RNA polymerase III.

In some embodiments, the technology described herein uses antisense nucleic acid (e.g., an antisense DNA oligo, an antisense RNA oligo) to modulate (e.g., inhibit) the expression of KLC1C. For example, in some embodiments, expression modulated (e.g., inhibited) using antisense compounds that specifically hybridize with one or more nucleic acids encoding KLC1C. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is modulation of the expression of KLC1C.

In some embodiments, methods are provided for inhibiting TEM. In some embodiments, methods are provided for inhibiting targeted recycling of the LBRC. In some embodiments, methods are provided to prevent/reduce migration of white blood cells into sites of inflammation. In some embodiments, such methods have no effect on adhesion of monocytes to the endothelial monolayers or migration of monocytes to the endothelial cell borders. In some embodiments, methods herein have no effect on constitutive recycling of the LBRC and only affects targeted recycling of the LBRC to the site of TEM.

In some embodiments, compositions and methods are provided for treating/preventing inflammation and diseases/conditions related thereto. In some embodiments, excess inflammation related to an injury/wound is inhibited/reduced. In some embodiments, chronic inflammation is treated/prevented. In some embodiments, acute inflammation is treated/prevented. In some embodiments, inflammation related to an autoimmune disorder (e.g., Rheumatoid arthritis) it treated/prevented. In some embodiments, methods/compositions are provided for treating/preventing inflammation related to asthma, chronic peptic ulcers, tuberculosis, chronic periodontitis, ulcerative colitis, Crohn's disease, chronic sinusitis, chronic active hepatitis, infections, wounds, tissue damage, cancer, atherosclerosis, periodontitis, allergies, multiple sclerosis, inflammatory bowel disease, dermatitis, interstitial lung disease, etc.

There are at least 45 kinesin family heavy chains, some with associated cargo-binding light chains, and all associated with specific cargo-binding adapter molecules. They all have important functions in cell physiology. In some embodiments, by targeting one splice variant of one specific light chain of one specific kinesin (e.g., KLC1C) all other kinesin-1 light chain 1 functions and all other microtubule molecular motor functions should be unaffected.

In some embodiments, various peptide/polypeptides are employed in embodiments herein. In some embodiments, a peptide/polypeptide described herein (e.g., KLC1C C-terminal peptide, KLC1C inhibitor peptide, etc.) is artificial. In some embodiments, a peptide/polypeptide described herein (e.g., KLC1C C-terminal peptide, KLC1C inhibitor peptide, etc.) is prepared by methods known to those of ordinary skill in the art. For example, the peptide can be synthesized using solid phase polypeptide synthesis techniques (e.g. Fmoc or Boc chemistry). Alternatively, the peptide can be produced using recombinant DNA technology (e.g., using bacterial or eukaryotic expression systems). Further, a peptide or polypeptide may be expressed within a subject (e.g., following administration of an appropriate vector). Accordingly, to facilitate such methods, provided herein are genetic vectors (e.g., plasmids, viral vectors (e.g. AAV), etc.) comprising a sequence encoding the peptide, as well as host cells comprising such vectors. Furthermore, provided herein are the peptides and polypeptides produced via such methods.

Embodiments are not limited to the specific peptide/polypeptide sequences listed herein. In some embodiments, peptides/polypeptides meeting limitations described herein and having substitutions not explicitly described are within the scope of embodiments here. In some embodiments, the peptides/polypeptides described herein are further modified (e.g., substitution, deletion, or addition of standard amino acids; chemical modification; etc.). Modifications that are understood in the field include N-terminal modification, C-terminal modification (which protects the peptide from proteolytic degradation), alkylation of amide groups, hydrocarbon "stapling" (e.g., to stabilize conformations). In some embodiments, the peptides/polypeptides described herein may be modified by conservative residue substitutions, for example, of the charged residues (K to R, R to K, D to E and E to D). Modifications of the terminal carboxy group include, without limitation, the amide, lower alkyl amide, constrained alkyls (e.g. branched, cyclic, fused, adamantyl) alkyl, dialkyl amide, and lower alkyl ester modifications. Lower alkyl is C1-C4 alkyl. Furthermore, one or more side groups, or terminal groups, may be protected by protective groups known to the ordinarily-skilled peptide chemist. The α-carbon of an amino acid may be mono- or dimethylated.

In some embodiments, any embodiments described herein may comprise mimetics corresponding to all or a portion of the peptides/polypeptides described herein (e.g., KLC1C C-terminal peptide, KLC1C inhibitor peptide, etc.), with various modifications that are understood in the field. In some embodiments, residues in the peptide sequences described herein may be substituted with amino acids having similar characteristics (e.g., hydrophobic to hydrophobic, neutral to neutral, etc.) or having other desired characteristics (e.g., more acidic, more hydrophobic, less bulky, more bulky, etc.). In some embodiments, non-natural amino acids (or naturally-occurring amino acids other than the standard 20 amino acids) are substituted in order to achieve desired properties.

In some embodiments, residues having a side chain that is positively charged under physiological conditions, or residues where a positively-charged side chain is desired, are substituted with a residue including, but not limited to: lysine, homolysine, δ-hydroxylysine, homoarginine, 2,4-diaminobutyric acid, 3-homoarginine, D-arginine, arginal (—COOH in arginine is replaced by —CHO), 2-amino-3-guanidinopropionic acid, nitroarginine (N(G)-nitroarginine), nitrosoarginine (N(G)-nitrosoarginine), methylarginine (N-methylarginine), ε-N-methyllysine, allo-hydroxylysine, 2,3-diaminopropionic acid, 2,2'-diaminopimelic acid, ornithine, sym-dimethylarginine, asym-dimethylarginine, 2,6-diaminohexinic acid, p-aminobenzoic acid and 3-aminotyrosine and, histidine, 1-methylhistidine, and 3-methylhistidine.

A neutral residue is a residue having a side chain that is uncharged under physiological conditions. A polar residue preferably has at least one polar group in the side chain. In some embodiments, polar groups are selected from hydroxyl, sulfhydryl, amine, amide and ester groups or other groups which permit the formation of hydrogen bridges.

In some embodiments, residues having a side chain that is neutral/polar under physiological conditions, or residues where a neutral side chain is desired, are substituted with a residue including, but not limited to: asparagine, cysteine, glutamine, serine, threonine, tyrosine, citrulline, N-methylserine, homoserine, allo-threonine and 3,5-dinitro-tyrosine, and β-homoserine.

Residues having a non-polar, hydrophobic side chain are residues that are uncharged under physiological conditions, preferably with a hydropathy index above 0, particularly above 3. In some embodiments, non-polar, hydrophobic side chains are selected from alkyl, alkylene, alkoxy, alkenoxy, alkylsulfanyl and alkenylsulfanyl residues having from 1 to 10, preferably from 2 to 6, carbon atoms, or aryl residues having from 5 to 12 carbon atoms. In some embodiments, residues having a non-polar, hydrophobic side chain are, or residues where a non-polar, hydrophobic side chain is desired, are substituted with a residue including, but not limited to: leucine, isoleucine, valine, methionine, alanine, phenylalanine, N-methylleucine, tert-butylglycine, octylglycine, cyclohexylalanine, β-alanine, 1-aminocyclohexylcarboxylic acid, N-methylisoleucine, norleucine, norvaline, and N-methylvaline.

In some embodiments, peptide and polypeptides are isolated and/or purified (or substantially isolated and/or substantially purified). Accordingly, in such embodiments, peptides and/or polypeptides are provided in substantially isolated form. In some embodiments, peptides and/or polypeptides are isolated from other peptides and/or polypeptides as a result of solid phase peptide synthesis, for example. Alternatively, peptides and/or polypeptides can be substantially isolated from other proteins after cell lysis from recombinant production. Standard methods of protein purification (e.g., HPLC) can be employed to substantially purify peptides and/or polypeptides. In some embodiments, the present invention provides a preparation of peptides and/or polypeptides in a number of formulations, depending on the desired use. For example, where the peptide/polypeptide is substantially isolated (or even nearly completely isolated from other proteins), it can be formulated in a suitable medium solution for storage (e.g., under refrigerated conditions or under frozen conditions). Such preparations may contain protective agents, such as buffers, preservatives, cryprotectants (e.g., sugars such as trehalose), etc. The form of such preparations can be solutions, gels, etc. In some embodiments, peptides and/or polypeptides are prepared in lyophilized form. Moreover, such preparations can include other desired agents, such as small molecules or other peptides, polypeptides or proteins. Indeed, such a preparation comprising a mixture of different embodiments of the peptides and/or polypeptides described here may be provided.

In some embodiments, provided herein are peptidomimetic versions of the peptide sequences described herein or variants thereof. In some embodiments, a peptidomimetic is characterized by an entity that retains the polarity (or non-polarity, hydrophobicity, etc.), three-dimensional size, and functionality (bioactivity) of its peptide equivalent but wherein all or a portion of the peptide bonds have been replaced (e.g., by more stable linkages). In some embodiments, 'stable' refers to being more resistant to chemical degradation or enzymatic degradation by hydrolytic enzymes. In some embodiments, the bond which replaces the amide bond (e.g., amide bond surrogate) conserves some properties of the amide bond (e.g., conformation, steric bulk, electrostatic character, capacity for hydrogen bonding, etc.). Chapter 14 of "Drug Design and Development", Krogsgaard, Larsen, Liljefors and Madsen (Eds) 1996, Horwood Acad. Publishers provides a general discussion of techniques for the design and synthesis of peptidomimetics and is herein incorporated by reference in its entirety. Suitable amide bond surrogates include, but are not limited to: N-alkylation (Schmidt, R. et al., Int. J. Peptide Protein Res., 1995, 46,47; herein incorporated by reference in its entirety), retro-inverse amide (Chorev, M. and Goodman, M., Acc. Chem. Res, 1993, 26, 266; herein incorporated by reference in its entirety), thioamide (Sherman D. B. and Spatola, A. F. J. Am. Chem. Soc., 1990, 112, 433; herein incorporated by reference in its entirety), thioester, phosphonate, ketomethylene (Hoffman, R. V. and Kim, H. O. J. Org. Chem., 1995, 60, 5107; herein incorporated by reference in its entirety), hydroxymethylene, fluorovinyl (Allmendinger, T. et al., Tetrahydron Lett., 1990, 31, 7297; herein incorporated by reference in its entirety), vinyl, methyleneamino (Sasaki, Y and Abe, J. Chem. Pharm. Bull. 1997 45, 13; herein incorporated by reference in its entirety), methylenethio (Spatola, A. F., Methods Neurosci, 1993, 13, 19; herein incorporated by reference in its entirety), alkane (Lavielle, S. et. al., Int. J. Peptide Protein Res., 1993, 42, 270; herein incorporated by reference in its entirety) and sulfonamido (Luisi, G. et al. Tetrahedron Lett. 1993, 34, 2391; herein incorporated by reference in its entirety).

As well as replacement of amide bonds, peptidomimetics may involve the replacement of larger structural moieties with di- or tripeptidomimetic structures and in this case, mimetic moieties involving the peptide bond, such as azole-derived mimetics may be used as dipeptide replacements. Suitable peptidomimetics include reduced peptides where the amide bond has been reduced to a methylene amine by treatment with a reducing agent (e.g. borane or a hydride reagent such as lithium aluminum-hydride); such a reduction has the added advantage of increasing the overall cationicity of the molecule.

Other peptidomimetics include peptoids formed, for example, by the stepwise synthesis of amide-functionalised polyglycines. Some peptidomimetic backbones will be readily available from their peptide precursors, such as peptides which have been permethylated, suitable methods are described by Ostresh, J. M. et al. in Proc. Natl. Acad. Sci. USA (1994) 91, 11138-11142; herein incorporated by reference in its entirety.

In some embodiments, the peptide/polypeptide described herein (e.g., KLC1C C-terminal peptide, KLC1C inhibitor peptide, etc.) are provided as fusions with other peptides or polypeptides. Such fusions may be expressed from a recombinant DNA which encodes the peptide/polypeptide described herein (e.g., KLC1C C-terminal peptide, KLC1C inhibitor peptide, etc.) and the additional peptide/polypeptide or may be formed by chemical synthesis. For instance, the fusion may comprise a cell-penetrating peptide (e.g., trans-activating transcriptional activator (TAT), antennapedia peptide, etc.), an enzyme of interest, a luciferase, RNasin or RNase, and/or a channel protein (e.g., ion channel protein), a receptor, a membrane protein, a cytosolic protein, a nuclear protein, a structural protein, a phosphoprotein, a kinase, a signaling protein, a metabolic protein, a mitochondrial protein, a receptor associated protein, a fluorescent protein, an enzyme substrate, a transcription factor, selectable marker protein, nucleic acid binding protein, extracellular matrix protein, secreted protein, receptor ligand, serum protein, a protein with reactive cysteines, a transporter protein, a targeting sequence (e.g., a myristylation sequence), a mitochondrial localization sequence, or a nuclear localization sequence. The functional peptide/polypeptide may be fused to the N-terminus and/or the C-terminus of the peptide/polypeptide described herein (e.g., KLC1C C-terminal peptide, KLC1C inhibitor peptide, etc.). In one embodiment, the fusion protein comprises a first peptide/polypeptide at the N-terminus and another (different) peptide/polypeptide at the C-terminus of the peptide/polypeptide described herein (e.g., KLC1C C-terminal peptide, KLC1C inhibitor peptide, etc.). Optionally, the elements in the fusion are separated by a connector sequence, e.g., preferably one having at least 2 amino acid residues, such as one having 13 and up to 40 or 50 amino acid residues. The presence of a connector sequence in a fusion protein of the invention does not substantially alter the function of either element in the fusion relative to the function of each individual element, likely due to the connector sequence providing flexibility (autonomy) for each element in the fusion. In certain embodiment, the connector sequence is a sequence recognized by an enzyme or is photocleavable. For example, the connector sequence may include a protease recognition site.

In some embodiments, provided herein are pharmaceutical compositions comprising of one or more peptide/polypeptide described herein (e.g., KLC1C C-terminal peptide, KLC1C inhibitor peptide, etc.) and a pharmaceutically acceptable carrier. Any carrier which can supply an active peptide or polypeptide (e.g., without destroying the peptide or polypeptide within the carrier) is a suitable carrier, and such carriers are well known in the art. In some embodiments, compositions are formulated for administration by any suitable route, including but not limited to, orally (e.g., such as in the form of tablets, capsules, granules or powders), sublingually, bucally, parenterally (such as by subcutaneous, intravenous, intramuscular, intradermal, or intrasternal injection or infusion (e.g., as sterile injectable aqueous or non-aqueous solutions or suspensions, etc.)), nasally (including administration to the nasal membranes, such as by inhalation spray), topically (such as in the form of a cream or ointment), transdermally (such as by transdermal patch), rectally (such as in the form of suppositories), etc.

Various delivery systems are known and may be used in certain embodiments to administer an inhibitor described herein (e.g. encapsulation in liposomes, microparticles, microcapsules, etc.). Methods of introduction include but are not limited to intradermal, intramuscular, intraperitoneal, intravenous, subcutaneous, intranasal, epidural, and oral routes. In some embodiments, inhibitors are administered by any convenient route, for example by infusion or bolus injection, by absorption through epithelial or mucocutaneous linings (e.g., oral mucosa, rectal and intestinal mucosa, etc.) and may be administered together with other biologically active agents (e.g., sequentially, simultaneously, separately-formulated, co-formulated, etc.). Administration may be systemic or local. In some embodiments, it is desirable to introduce the inhibitors into the circulation system by any suitable route. Pulmonary administration may also be employed (e.g., by use of an inhaler or nebulizer, and formulation with an aerosolizing agent).

In some embodiments, inhibitors are administered locally to the area in need of treatment; this may be achieved, for example and not by way of limitation, by topical application, by injection, by means of a catheter, by means of a suppository, or by means of an implant, said implant being of a porous, non-porous, or gelatinous material, including membranes, such as sialastic membranes, or fibers.

"Effective amount" refers to the amount or dose of the inhibitor, upon single or multiple dose administration to the patient, which provides the desired effect in the patient under treatment. An effective amount can be readily determined by the attending diagnostician, as one skilled in the art, by the use of known techniques and by observing results obtained under analogous circumstances. In determining the effective amount or dose of agent administered, a number of factors are considered by the attending diagnostician, including, but not limited to: the species of mammal; its size, age, and general health; the specific disease involved; the degree of or involvement or the severity of the disease; the response of the individual patient; the particular inhibitor administered; the mode of administration; the bioavailabilty characteristics of the preparation administered; the dose regimen selected; the use of concomitant medication; and other relevant circumstances.

The term "carrier" refers to a diluent, adjuvant, excipient, or vehicle with which the compound or pro-drug of the invention is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol and water. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the USP7 inhibitor (compound or pro-drug of the invention), preferably in purified form, together with a suitable amount of carrier so as to provide the form for proper administration to the patient. The formulation should suit the mode of administration.

Typically, compositions for intravenous administration are solutions in sterile isotonic aqueous buffer. Where necessary, the composition may also include a solubilizing agent and a local anesthetic such as lignocaine to, ease pain at the, site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline.

In various embodiments, the bioactive agent (e.g., peptide, antibody, small molecule, etc.) is administered in an amount, on a schedule, and for a duration sufficient to decrease triglyceride levels by at least 5%, 10%, 15%, 20% or 25% or more as compared to levels just prior to initiation of treatment. In some embodiments, the bioactive agent is administered in an amount, on a dosage schedule, and for a duration sufficient to decrease oxalate levels (e.g., in urine, in plasma) by at least 10%, 15%, 20%, 25%, 30%, 35%, 40%, 45% or 50%. In particular embodiments, the bioactive agent is administered in an amount, on a schedule, and for a time sufficient to decrease oxalate levels (e.g., in urine, in plasma) by at least 55%, 60%, 65%, even at least about 70% or more.

In certain embodiments, the bioactive agent (e.g., peptide, antibody, small molecule, etc.) is administered in an amount, expressed as a daily equivalent dose regardless of dosing frequency, of 50 micrograms ("mcg") per day, 60 mcg per day, 70 mcg per day, 75 mcg per day, 100 mcg per day, 150 mcg per day, 200 mcg per day, or 250 mcg per day. In some embodiments, the bioactive agent is administered in an amount of 500 mcg per day, 750 mcg per day, or 1 milligram ("mg") per day. In yet further embodiments, the bioactive agent is administered in an amount, expressed as a daily equivalent dose regardless of dosing frequency, of 1-10 mg per day, including 1 mg per day, 1.5 mg per day, 1.75 mg per day, 2 mg per day, 2.5 mg per day, 3 mg per day, 3.5 mg per day, 4 mg per day, 4.5 mg per day, 5 mg per day, 5.5 mg per day, 6 mg per day, 6.5 mg per day, 7 mg per day, 7.5 mg per day, 8 mg per day, 8.5 mg per day, 9 mg per day, 9.5 mg per day, or 10 mg per day.

In various embodiments, a bioactive agent (e.g., peptide, antibody, small molecule, etc.) is administered on a monthly dosage schedule. In other embodiments, the bioactive agent is administered biweekly. In yet other embodiments, the bioactive agent is administered weekly. In certain embodiments, the bioactive agent is administered daily ("QD"). In select embodiments, the bioactive agent is administered twice a day ("BID").

In typical embodiments, a bioactive agent (e.g., peptide, antibody, small molecule, etc.) is administered for at least 3 months, at least 6 months, at least 12 months, or more. In some embodiments, the bioactive agent is administered for at least 18 months, 2 years, 3 years, or more.

In some embodiments, methods and compositions are provided for co-administration of a bioactive agent (e.g., peptide, antibody, small molecule, etc.) with one or more additional pharmaceutical agents. In some embodiments, an additional agent is an anti-inflammatory agent (e.g., Non-steroidal anti-inflammatory drug (NSAID), corticosteroids, etc.).

EXPERIMENTAL

Example 1

Materials and Methods

Cells and Plasmid Constructs

HUVEC were isolated as described in ref. 18 (herein incorporated by reference in its entirety). They were grown on collagen and fibronectin, in M199 medium (which includes bicarbonate and HEPES) supplemented with 20% human serum and 5% penicillin/streptomycin (ref 19; herein incorporated by reference in its entirety).

Figure 6A:
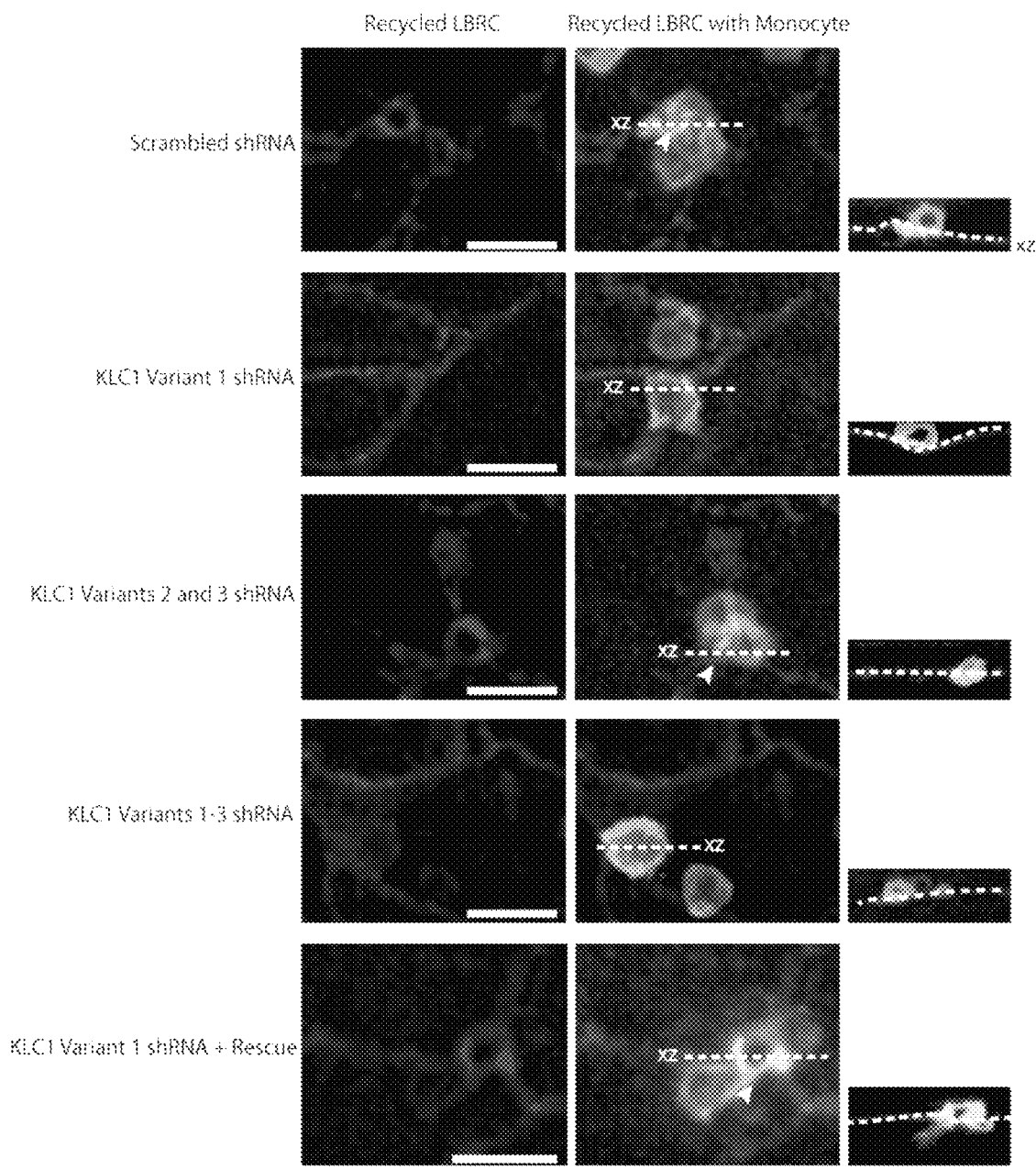
FIGS. 6A-6C. Knockdown of KLC1 isoform variant 1 in HUVEC results in a decrease in LBRC targeted recycling. HUVEC were transduced with Scrambled shRNA, KLC1 Variant 1 shRNA, KLC1 Variants 2 & 3 shRNA, and KLC Variants 1-3 shRNA. Monocytes were allowed to transmigrate for 8.5 minutes. A) Confocal stacks were imaged and B) LBRC enrichment was measured around all adherent monocytes. C) Targeted recycling was significantly decreased upon knockdown of KLC1 isoform variant 1. Arrowheads indicate site of leukocyte TEM. Dotted lines in the orthogonal projection indicate abluminal surface of endothelial cells. Scale bar=10 µm.
Figure 6B:
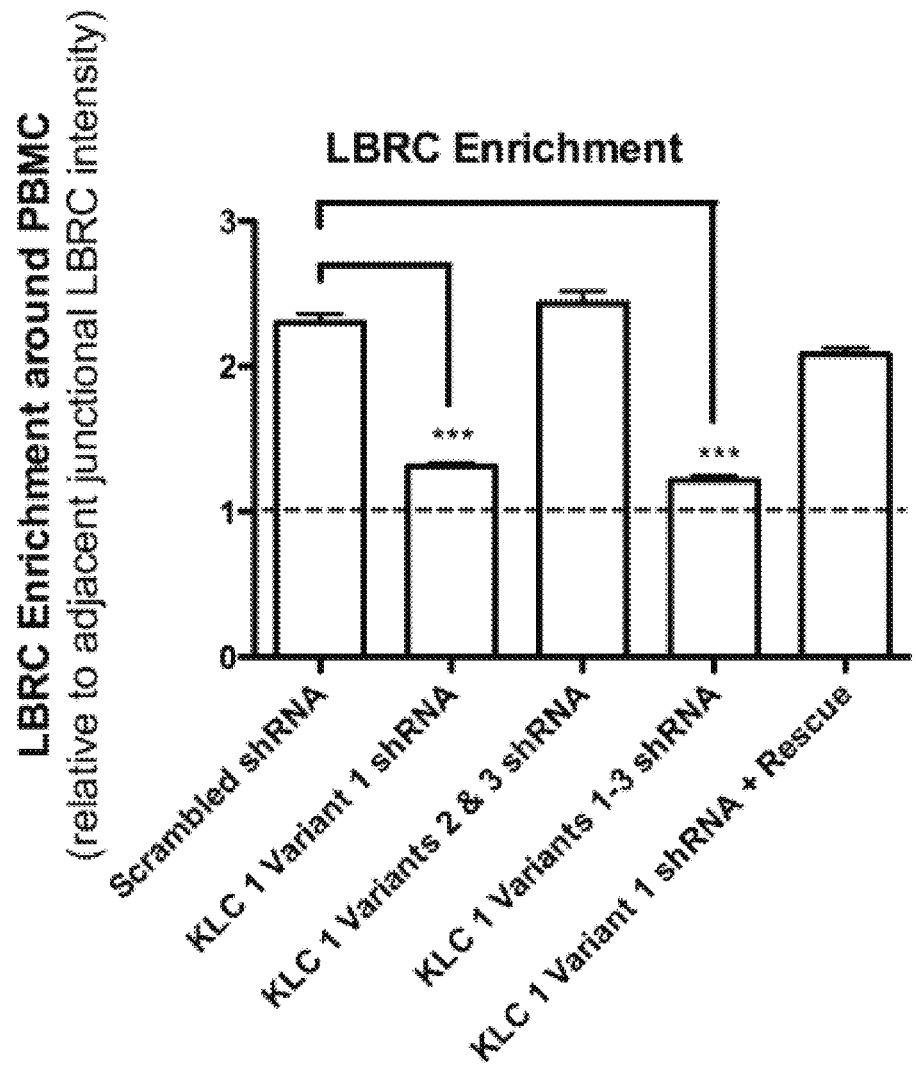
Figure 6C:
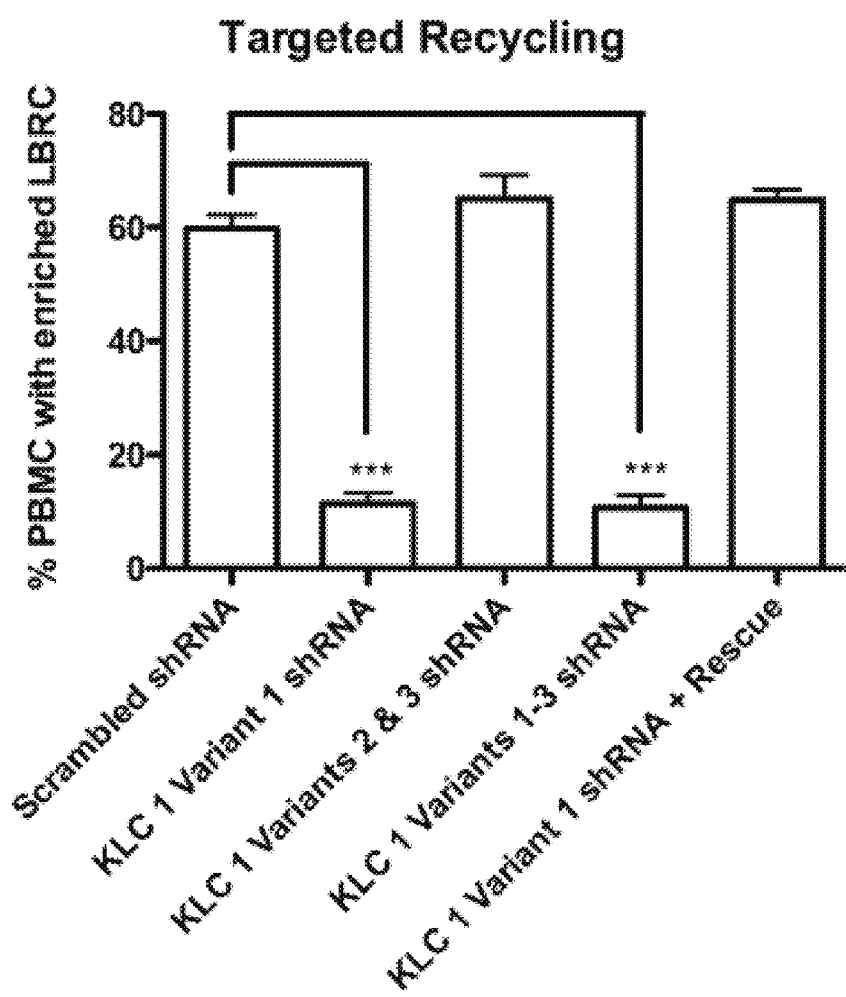

The Kinesin-1 (NM_004521) knockdown sequences were as follows: 5'-CTCAAGAGCAAGTGTATAAT-3' (SEQ ID NO: 9) and 5'-AAAGATGTACTTGAAGGATAT-3' (SEQ ID NO: 10). The KHC rescue construct was made with silent point mutations in the targeted sequences, and cloned into the vector containing an in-frame mCherry tag at the 3' end to distinguish the rescue construct from endogenous Kinesin-1 (FIG. 6). The KLC shRNAs were made to target the 3' noncoding region of the respective mRNAs. The sequences are as follows: KLC1 isoform variant 1 (NM_005552.4)-5'-TGTATTTGTGTCTTTCTAA-3' (SEQ ID NO: 11); KLC1 isoform variants 2 (NM_182923.3) and 3 (NM_001130107.1)-5'-GCATAGGACATGATACTAA-3' (SEQ ID NO: 12). The KLC 1 isoform variant 1 was rescued by KLC1 variant 1 cDNA (Vigene Biosciences).

Antibodies

SUK4 (anti-Kinesin-1) hybridoma cell line and K2.4 (anti-Kinesin-2) ascites were from Dr. Vladimir Gelfand (Northwestern University). Rabbit mAb against KLC1 was purchased from Abcam. Rabbit pAb against KLC2 was purchased from Pierce-Antibodies. Unlabeled and Alexa-568-conjugated goat anti-mouse F(ab')$_2$ antibodies from Jackson ImmunoResearch Laboratories and Life Technologies were used for targeted recycling experiments to label recycling PECAM. Hec1 (anti-VE-cadherin), hec7 (anti-CD31), P1.1 (anti-CD31), IB4 (anti-CD18), and hec2 (anti-CD99) were used as previously described (refs. 5,20; herein incorporated by reference in their entireties). Anti-α-tubulin antibody was purchased from Accurate Chemical.

Transduction of HUVEC with Adenovirus 293A cells were grown on 100 mm dishes to 70-90% confluency and then transfected with adenoviral constructs using Lipofectamine 2000 for delivery. Amplified virus that expressed KHC and KLC knockdown and rescue constructs was purified and used to in transduction of HUVEC for knockdown and rescue experiments (VIRAPOWER Adenoviral Expression System).

SDS-PAGE and Western Blotting

HUVEC were harvested for SDS-PAGE by washing with PBS and adding sample buffer. DNA was sheared by passing through a 27 G needle 10 times and samples were heated to 100° C. for 5 minutes. Samples were separated on 8% polyacrylamide gels and transferred onto polyvinyldifluoride membranes before blocking with 5% milk in PBS with 0.05% Tween and probing with primary antibodies. Blots were incubated with horseradish peroxidase-conjugated secondary antibodies in 5% milk in PBS with 0.05% Tween, then washed, and detected using chemiluminescence and exposure to X-ray film.

Microinjection into HUVEC

HUVEC were plated at 30,000 cells per Mattek dish in M199 medium supplemented with 20% human serum, 5% penicillin/streptomycin, and bicarbonate for 2 days prior to microinjection. On the day of microinjection, HUVEC were activated with TNF-α (20 ng/ml) and media was exchanged to M199 without bicarbonate and supplemented with 20% FBS. A working concentration of 5 mg/ml of SUK4 mouse mAb, pre-immune mouse IgG isotype control, and K2.4 were mixed with 1 mg/ml Dextran-Alexa 488 for microinjection to tag injected cells. Microinjection was performed under an Olympus DSU microscope (20× phase contrast lens), using an Eppendorf FemtoJet Microinjector and Micromanipulator. Cells were kept at 37° C. during microinjection. Microcapillaries were pulled using a Sutter Instrument Company P-97 Flaming/Brown Micropipette Puller. A field of approximately 100 contiguous HUVEC was microinjected with the SUK4 mAb. After microinjection, HUVEC media was exchanged back to conditioned M199 medium with 20% human serum, 5% penicillin/streptomycin, and bicarbonate, and then placed in a 37° C. $CO_2$ incubator to allow for HUVEC to recover for at least one hour before conducting targeted recycling assays.

Transendothelial Migration (TEM) Assay

The TEM assay is a quantitative assay designed to assess, using large numbers of transmigration events (more than 300 per variable tested), the effect of various treatments such as knocking down Kinesin-1, on the process of transmigration. As routinely performed in our lab (refs. 19,21; herein incorporated by reference in their entireties), peripheral blood mononuclear cells (PBMC, to assess monocyte transmigration) from healthy volunteers are purified on a Ficoll density gradient and then washed in Hanks' buffered saline solution (HBSS) plus 0.1% human serum albumin. Following this wash, they are resuspended in Medium 199 plus 0.1% human serum albumin. $2 \times 10^6$ cells are added to confluent TNF-α activated (10 ng/mL, >4 hrs) human umbilical vein endothelial cell (HUVEC) monolayers grown on hydrated collagen gels and incubated for 1 h at 37° C. in a $CO_2$ incubator (ref. 22; herein incorporated by reference in its entirety). This is enough time to allow maximum TEM of control cells (~90%).

To assess the role of microtubule motors in leukocyte TEM, control and experimentally treated HUVEC are compared side by side in this assay. The co-culture is washed with cold PBS and fixed overnight with 2.5% glutaraldehyde in 0.1 M sodium cacodylate buffer, pH 7.4. TEM is quantitated by Nomarski optics (ref. 21; herein incorporated by reference in its entirety). To image, the cells plated on collagen gels in 96-well plates were transferred onto glass slides and visualized by a Zeiss Axiophot2 microscope, with a 60× oil immersion objective. Adherent monocytes are those in the same focal plane as the endothelial monolayer. Transmigrated monocytes are those in a focal plane below the monolayer. Monocytes are scored in each of several random fields for each monolayer until at least 100 are counted, with 3 replicate monolayers for each condition for a total of over 300 cells per variable tested. To avoid unintentional bias, all cells in the field are counted. Data are expressed as the percent of total leukocytes (attached plus transmigrated) that have transmigrated.

Targeted Recycling Assay

The Targeted Recycling assay determines whether the LBRC has been recruited to transmigrating leukocytes. Targeted recycling was performed as described previously (ref 5; herein incorporated by reference in its entirety). HUVEC monolayers are incubated with an Fab fragment of P1.1 mAb for 1 h at 37° C. in a $CO_2$ incubator. P1.1 binds to PECAM domain five and does not interfere with any known function of PECAM (ref. 23; herein incorporated by reference in its entirety). HUVEC are then put on ice and washed with PBS to remove any free unbound Fab, followed by an incubation with an excess of F(ab')2 fragment of unlabeled goat anti-mouse IgG on ice for 1 h. This saturably binds all of the Fab that is present on the surface of the endothelial junction, but will not enter the LBRC at this temperature. Free antibody is washed away and $2 \times 10^6$ PBMCs mixed with Alexa-568-conjugated F(ab')2 fragment of the same goat anti-mouse antibody are added to the cells for 20 min on ice and then transferred to the $CO_2$ incubator for 8 minutes to allow for synchronized transmigration to begin. Cells are then put on ice and washed with ice-cold PBS, followed by fixation in 2% paraformaldehyde for 10 min at room temperature.

Since the P1.1 mAb does not interfere with PECAM function, tracking it serves as a surrogate marker for the movement of the LBRC. In this procedure, only PECAM that was originally in the LBRC and recycled to the surface during the transmigration period will be labeled with the fluorescent secondary antibody, since it was protected from the unlabeled secondary antibody during the incubation on ice. The synchronized transmigration for a short time (8 minutes) catches leukocytes early in the act of transmigration before significant constitutive recycling and a corresponding increase in the staining of uninvolved junction occurs.

Confocal fluorescence microscopy is used to image the targeted recycling events. Leukocytes are identified with fluorescently conjugated mAb against CD18 (IB4). Diapedesis is determined by demonstration of leukocytes traversing the endothelial monolayer as seen on multiple sequential focal planes and using an orthogonal projection. The number of monocytes in contact with the endothelial monolayer at cell junctions was assessed, and of those, it was determined how many are contacted by membrane from the LBRC. The intensity of fluorescent Goat-anti-mouse mAb was measured to quantify enrichment of recycling LBRC around transmigrating leukocytes. One-pixel-wide lines are drawn along the area surrounding the site of diapedesis. The mean fluorescence intensity in contact with the leukocyte is divided by the average intensity of constitutively recycled PECAM at the adjacent cell border to calculate LBRC enrichment around transmigrating leukocytes. Multiple monolayers were examined until at least one hundred transmigration events are observed for each variable tested. To avoid unintentional bias each leukocyte in contact with the endothelial border is scored, whether or not it has initiated TEM. For imaging, the cells plated on collagen gels in 96-well plates were transferred onto 35 mm glass bottom dishes and imaged on a Perkin Elmer UltraVIEW VoX Confocal Spinning Disk Microscope, using appropriate filters for visualizing Alexa 488, Alexa 568, and Dylight 650 conjugated probes (Thermo Fisher Scientific). Images were acquired using a UPlanApo 40× oil immersion objective and Volocity software (Perkin Elmer). Image processing and quantification of data are performed using Volocity and ImageJ (NIH) image processing software.

Statistics

All data are analyzed by pairwise comparison using a two-tailed t test assuming unequal variances, with the Bonferroni correction for multiple comparisons as appropriate.

Example 2

Results

Blocking Kinesin-1 with SUK4 Inhibits Paracellular TEM

There are 45 KIF genes that encode 45 kinesin heavy chains. There are multiple associated light chains in the human genome (refs. 24,25; herein incorporated by reference in their entireties). Experiments conducted during development of embodiments herein focused first on Kinesin-1 as a candidate to mediate targeted recycling of the LBRC. Three genes, KIFA, KIFB, and KIFC encode three variants of Kinesin-1 differing only at their C-terminal ends (1,028, 962, and 956 amino acids, respectively) (refs. 25,26; herein incorporated by reference in their entireties). Human umbilical vein endothelial cells (HUVEC) express the ubiquitous KIF5B isoform as well as KIF5C, but not KIF5A (ref. 6; herein incorporated by reference in their entireties). To study the role of Kinesin-1 in TEM, a function-blocking monoclonal antibody specific for Kinesin-1 (SUK4) that recognizes both KIF5B and KIF5C isoforms 27, 28 or isotype control mouse IgG was microinjected into confluent HUVEC monolayers and conducted TEM assays. Unlike the HD anti-kinesin antibody (ref. 6; herein incorporated by reference in its entirety), SUK4 is specific for kinesin-1 and does not recognize other members of the kinesin motor superfamily (ref. 27; herein incorporated by reference in its entirety). Furthermore, although it was originally raised against sea urchin Kinesin-1, it has been proven to be cross-reactive with mammalian Kinesin-1 (refs 29-31; herein incorporated by reference in their entireties).

Figure 1B:
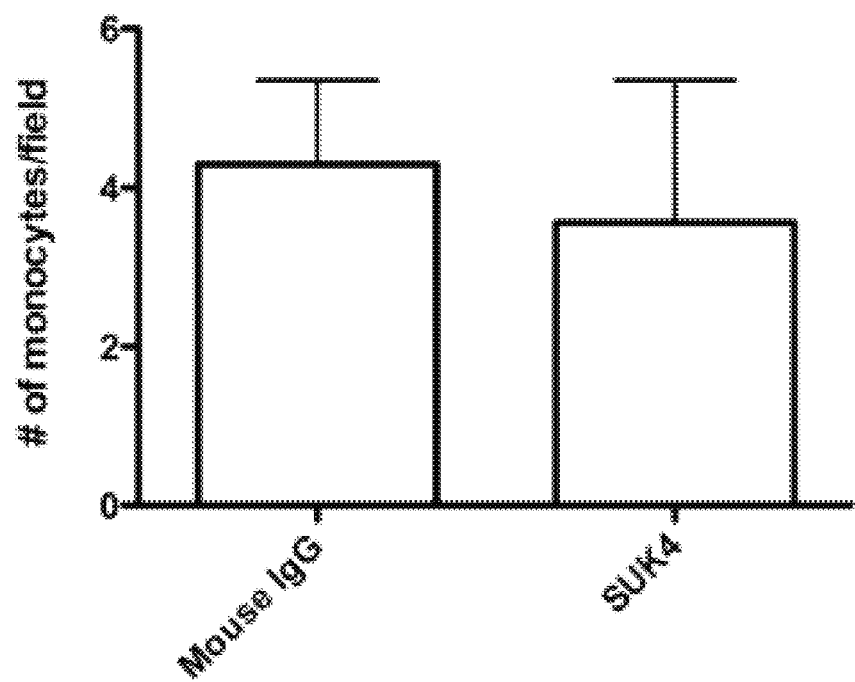
Figure 1C:
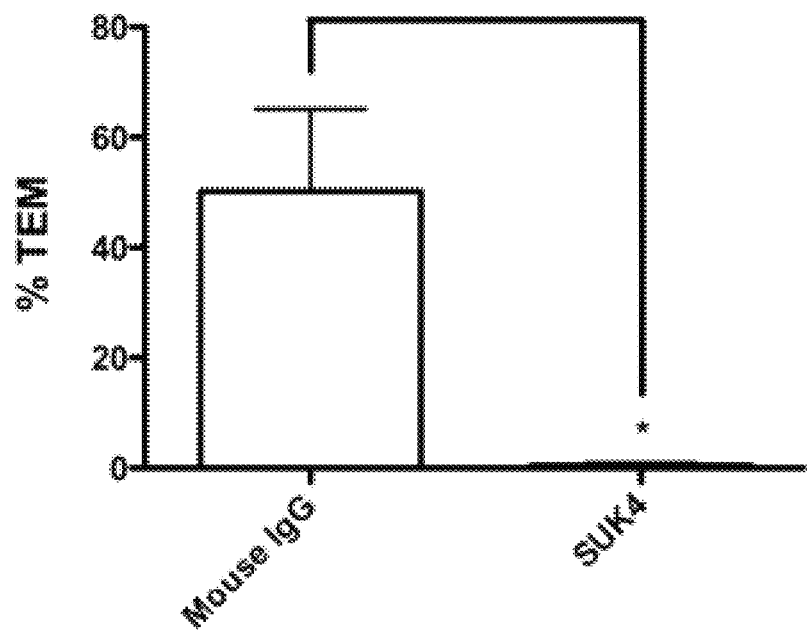

The microinjected monolayers remained intact, and monocytes were able to attach and migrate (FIG. 1A). There was no difference in the ability of the monocytes to adhere to the mouse IgG-injected endothelial cells compared with those of the SUK4-injected endothelial cells (FIG. 1B). Within 8 minutes approximately 50% of adherent monocytes were already undergoing TEM across HUVEC injected with isotype-matched mouse IgG. In contrast, transmigration was ablated in the SUK4 injected HUVEC (FIG. 1C), indicating a role for Kinesin-1 in leukocyte TEM.

Blocking Kinesin-1 with SUK4 Inhibits Targeted Recycling of the LBRC

Targeted recycling assays were performed to determine if Kinesin-1 is necessary for targeting the LBRC to the site of TEM. The LBRC constitutively recycles evenly around the endothelial cell with a half time of 10 minutes. When leukocytes transmigrate, even though constitutive recycling still occurs somewhat evenly along the cell borders, LBRC membrane in their vicinity preferentially traffics toward them (targeted recycling), resulting in enhanced fluorescence at the site of TEM in these assays (refs. 5,6; herein incorporated by reference in their entireties). In these experiments, transmigration is allowed to proceed for a short time (7-8 minutes) in order to observe the interaction of recycling LBRC with leukocytes as they transmigrate (ref. 5; herein incorporated by reference in its entirety) and before fluorescence associated with constitutive recycling catches up.

Figure 1D:
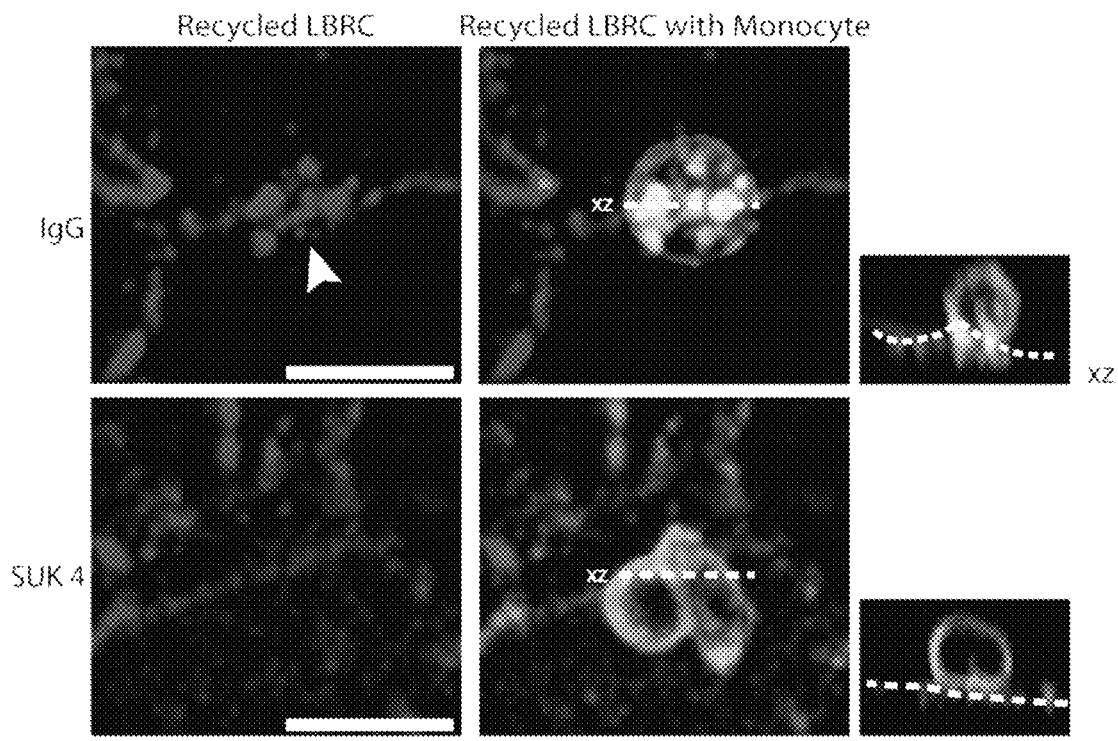
Figure 1E:
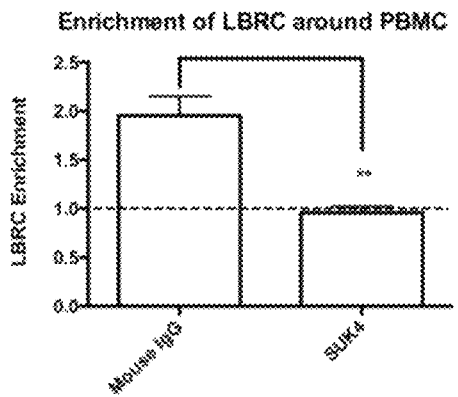
Figure 1F:
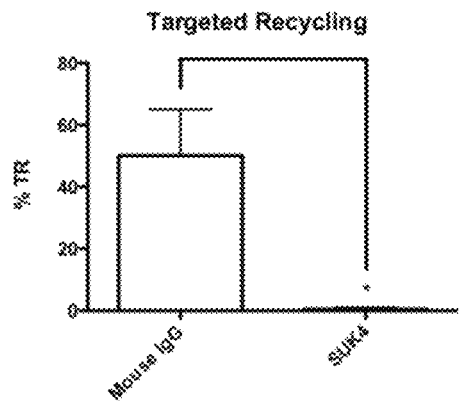
Figure 1G:
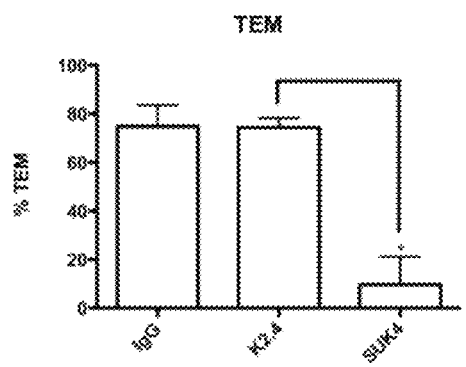

The average intensity of the recycled LBRC fluorescence was measured around all the monocytes at the junctions and compared to the average intensity of constitutively recycled LBRC fluorescence along the neighboring junction (arbitrarily set at 1.0). In order to avoid unintentional bias, the intensity of recycling LBRC was quantified under or around every leukocyte situated at a junction (including about half of them that have not begun transmigration). This is expressed as "LBRC enrichment" in the figure and is a measure of the entire population of bound leukocytes. A two-fold average enrichment of the LBRC in contact with transmigrating PBMC was observed in the mouse IgG isotype control injected HUVEC. This appears as a ring or crescent around the transmigrating leukocyte, but sometimes as small patches where the leukocyte engages the EC border (FIG. 1D). In contrast, HUVEC microinjected with the SUK4 mAb did not support TEM (FIG. 1B) and showed no increase in recycling of the LBRC associated with leukocytes adherent to their cell borders (FIGS. 1, D and E). The percentage of monocytes associated with enhanced LBRC recycling (≥2-fold compared to adjacent junctions) is denoted as "percent targeted recycling." At this early time point only about 50% of the monocytes were undergoing TEM in control co-cultures, but virtually all of them were associated with enhanced trafficking of LBRC membrane (targeted recycling) (FIG. 1F). Targeted recycling was ablated when HUVEC were microinjected with SUK4 (FIG. 1F). This indicates that Kinesin-1 facilitates targeting the LBRC to the site of TEM. As an additional control for specificity, K2.4, a monoclonal antibody against Kinesin-2 (ref. 32; herein incorporated by reference in its entirety) was microinjected in parallel with SUK4 and isotype control. Only SUK4 blocked TEM (FIG. 1G).

shRNA Knockdown of Kinesin-1 Inhibits Paracellular TEM

Figure 3A:
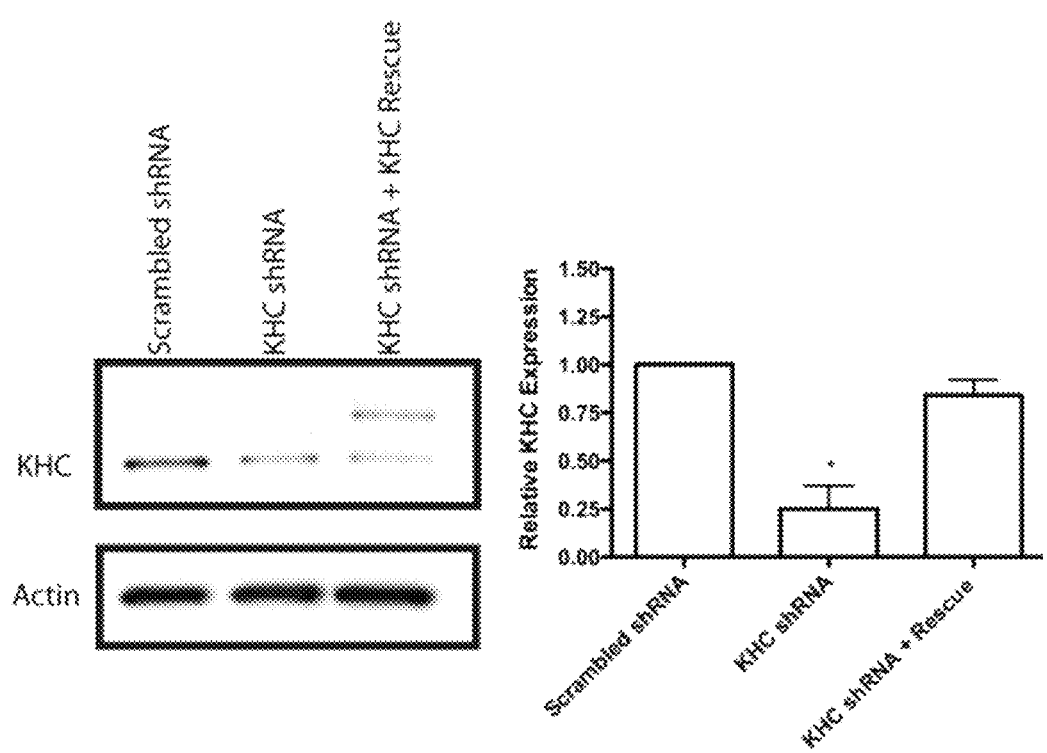
FIGS. 3A-3E. Knockdown of Kinesin-1 blocks TEM. A) Western Blot was performed 72 hours postinfection with scrambled shRNA, Kinesin-1 shRNA (KHC shRNA), or Kinesin-1 shRNA with addition of the Kinesin-1 rescue construct tagged with mCherry (upper band in KHC shRNA+Rescue lane). A polyclonal antibody against Kinesin-1 was used to probe for KHC. Relative total KHC expression is quantified to the right of the blot. B) Following knockdown of Kinesin-1, cells were stained for VE-cadherin, PECAM, and microtubules. Inset images for microtubules show enlargements of a portion (denoted by a dotted outline of a rectangular box) of the stained images for clarity. PBMC were allowed to transmigrate on infected HUVEC monolayers for 8.5 minutes before quantifying C) adhesion and D) migration to cell borders. E) PBMC were allowed to transmigrate on HUVEC monolayers for 60 minutes to measure TEM.
Figure 3B:
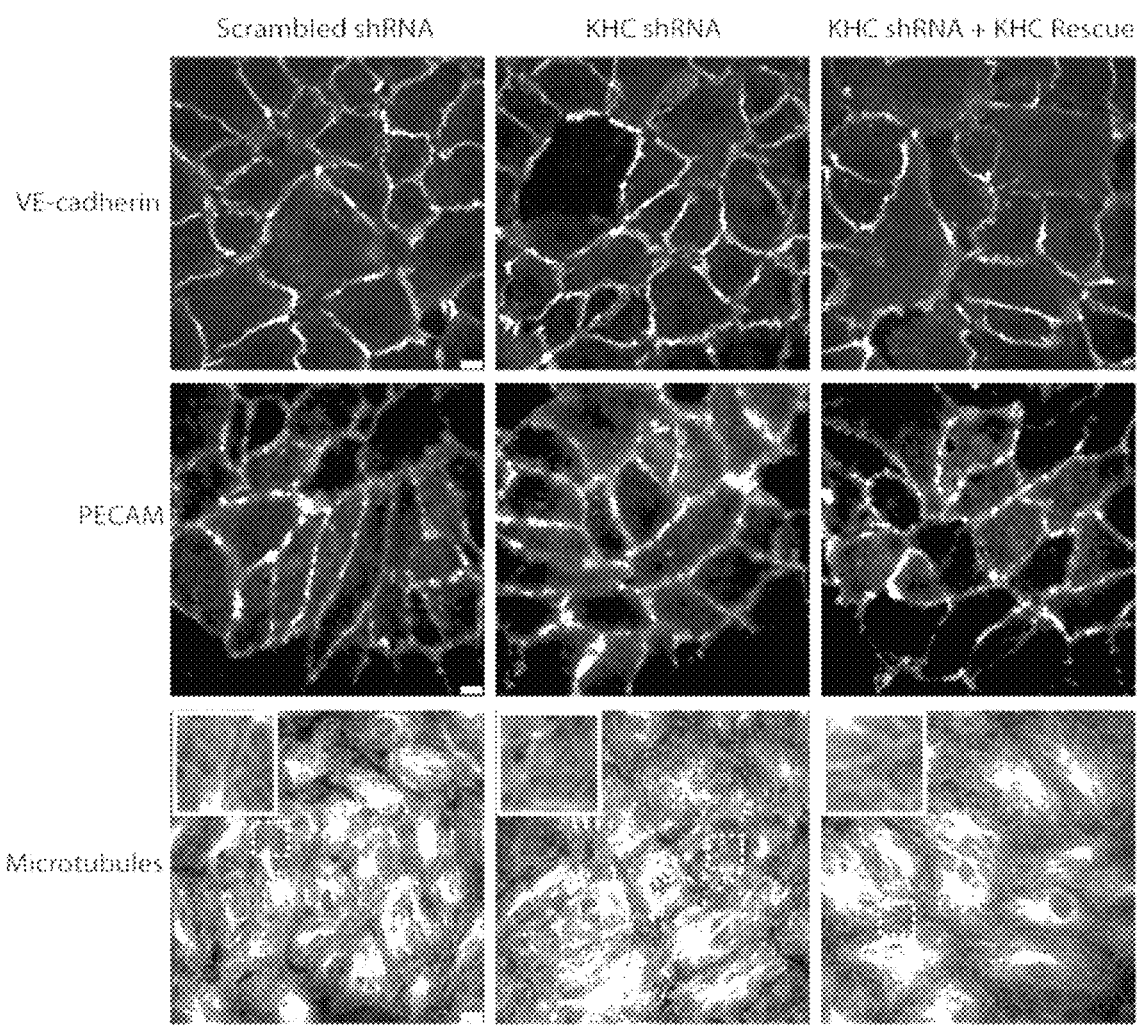

In a complementary approach, Kinesin-1 was specifically knocked down in endothelial cells. There are three genes for Kinesin-1 in mammals: KIF5A, KIF5B, and KIF5C (refs. 24,25; herein incorporated by reference in their entireties). Since KIF5A is not expressed in HUVEC and KIF5C was detected by PCR, but not immunofluorescence, KIF5B was focused on, which is strongly expressed in HUVEC (ref 6; herein incorporated by reference in its entirety). Two KIF5B shRNA knockdown constructs were cloned into destination vectors for adenoviral expression. Other than a slight overlap, the target sequences for KIF5B do not match sites on KIF5A or KIF5C sequences. The amplified virus was used to transduce HUVEC (refs. 33,34; herein incorporated by reference in their entireties). Western Blot analysis of virally-transduced HUVEC was used to quantify knockdown of Kinesin-1. A 75 percent knockdown of Kinesin-1 was measured 72 hours postinfection with the shRNA-expressing adenovirus, and knockdown was rescued after addition of the wildtype Kinesin-1 adenovirus construct that was tagged with mCherry to distinguish it from residual endogenous Kinesin-1 and mutated to prevent it from being targeted by the Kinesin-1 shRNA (FIGS. 2 and 3A). Knockdown of Kinesin-1 did not affect the distribution of microtubules, or the expression levels or distribution of VE-cadherin or PECAM (FIG. 3B).

Figure 3C:
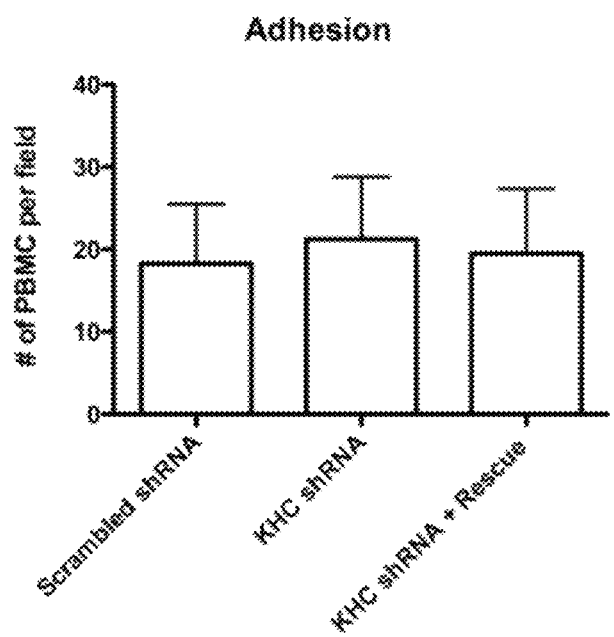
Figure 3D:
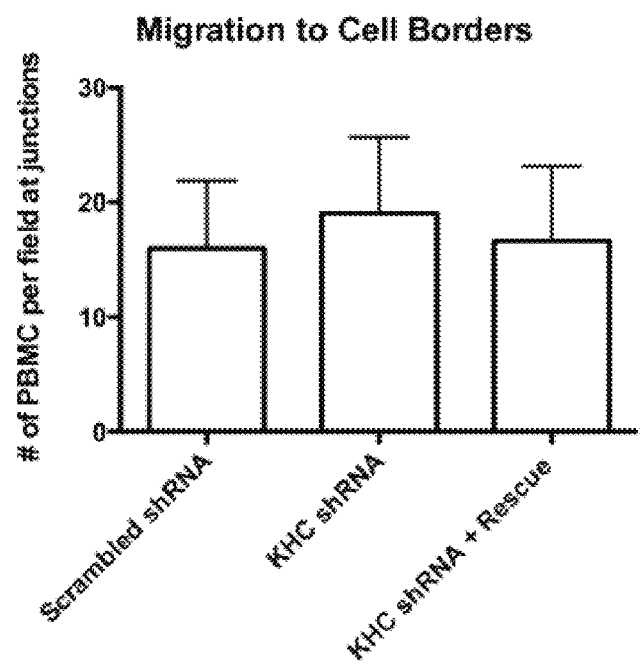
Figure 3E:
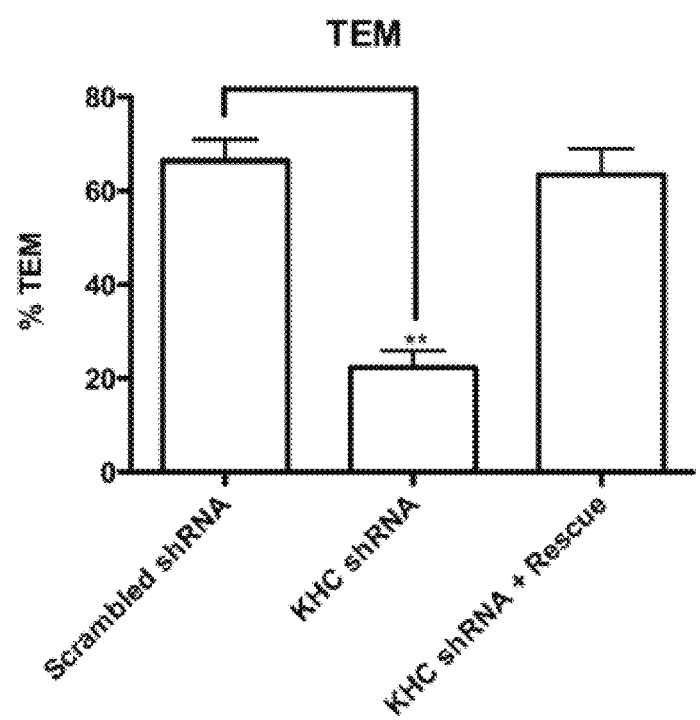

Knockdown of Kinesin-1 in EC did not affect the number of monocytes attached to HUVEC monolayers, showing that knocking down Kinesin-1 in HUVEC does not affect adhesion of monocytes prior to TEM (FIG. 3C). Likewise, there was also no difference in the average number of monocytes at HUVEC junctions between control and knockdown cells, indicating that Kinesin-1 is not required for migration of monocytes to cell borders prior to TEM (FIG. 3D). However, knockdown of Kinesin-1 in HUVEC did result in a significant decrease in transmigration of monocytes in our standard one hour TEM assay, supporting our microinjection results. TEM was rescued upon transduction with the Kinesin-1 rescue construct (FIG. 3E).

shRNA Knockdown of Kinesin-1 Inhibits Targeted Recycling of the LBRC

Figure 4A:
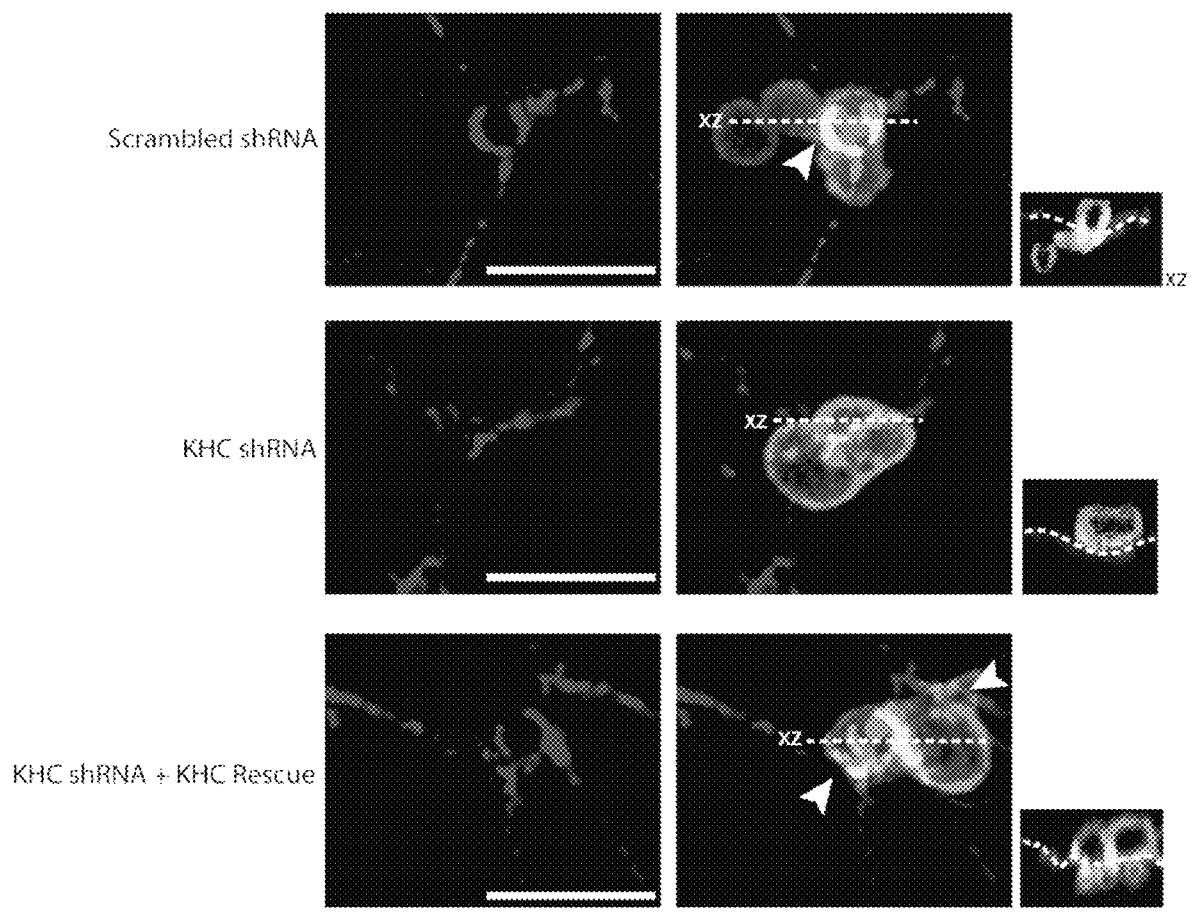
FIGS. 4A-4C. Knockdown of Kinesin-1 in HUVEC results in a decrease in LBRC targeted recycling. HUVEC were transduced with scrambled shRNA, Kinesin-1 shRNA (KHC shRNA), or Kinesin-1 shRNA with addition of the Kinesin-1 rescue construct (KHC shRNA+Rescue). Monocytes were allowed to transmigrate for 8.5 minutes. A) Confocal stacks were imaged, with CD18 and recycled LBRC. Orthogonal images on the far right indicate whether the monocyte is in the process of transendothelial migration or engaging the endothelial cell border. Arrowheads indicate site of leukocyte TEM. Dotted lines in the orthogonal projection indicate abluminal surface of endothelial cells. Constitutive recycling occurs, including under the blocked leukocyte (refs. 5,6; herein incorporated by reference in their entireties), when kinesin-1 is knocked down, but there is no enrichment of LBRC around the monocyte. The KHC shRNA+Rescue panel shows two transmigrating monocytes, one exhibiting a ring of enrichment surrounding it and the other exhibiting local enrichment at both sides of it as in FIG. 1D. B) LBRC enrichment was measured around all adherent monocytes. C) Targeted recycling was significantly decreased upon knockdown of KLC1, and restored to control levels with the rescue. Scale bar=10 µm.
Figure 4B:
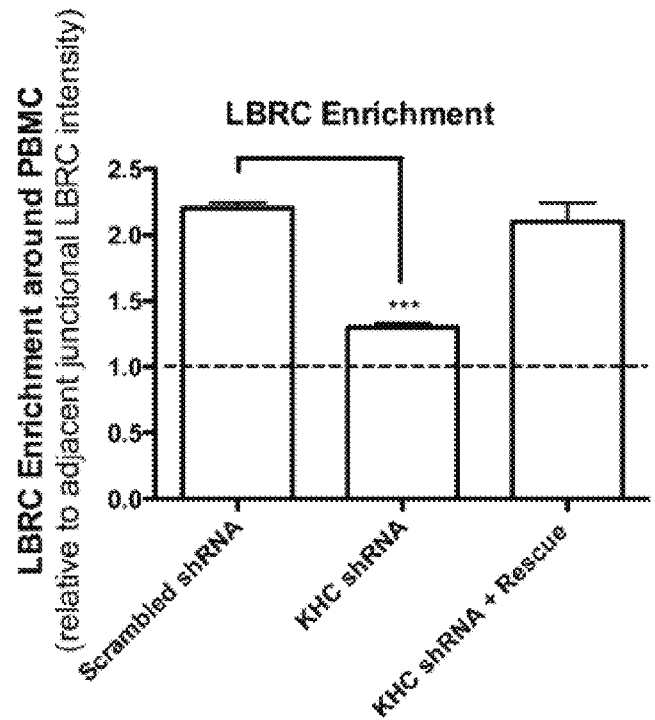
Figure 4C:
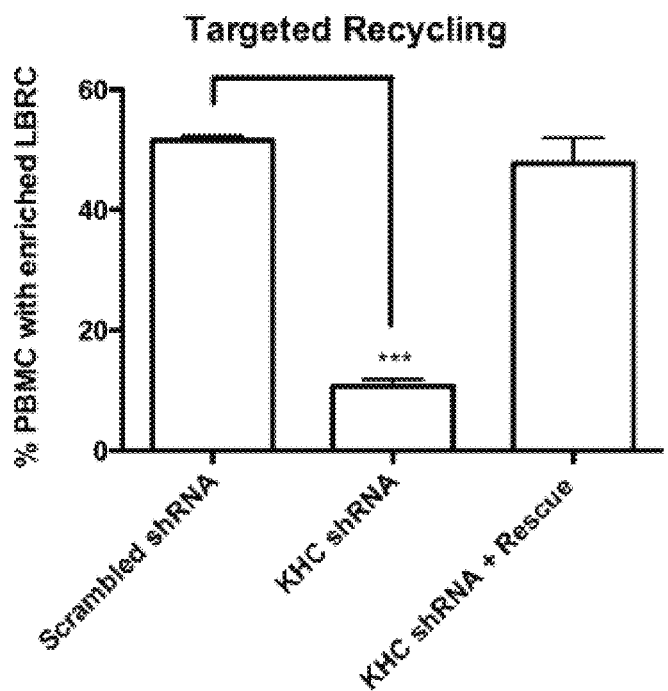

The effect of KHC knockdown on targeted recycling was examined. In cells transduced with scrambled shRNA, membrane recycled from the LBRC and was detected as a rim of enriched fluorescence around monocytes "caught in the act" of TEM (FIG. 4A). Upon knockdown of Kinesin-1 in HUVEC, concomitant with the block in TEM, there was virtually no enrichment of the LBRC surrounding monocytes at endothelial junctions, although constitutive recycling occurred under the blocked monocytes (FIG. 4A). Re-expression of Kinesin-1 with a rescue cDNA construct restored targeted recycling to control levels (FIG. 4B). Recycling LBRC was labeled with Alexa-488 to avoid interference by the mCherry tag of the rescue construct. Targeted recycling of the LBRC was significantly decreased upon knockdown of Kinesin-1 (FIG. 4C). Together, these data indicate that Kinesin-1 function a key component in the targeted recycling, and hence, transendothelial migration.

Knockdown of Kinesin-1 Light Chain 1 Variant 1 Inhibits TEM

Figures 5A, 5B:
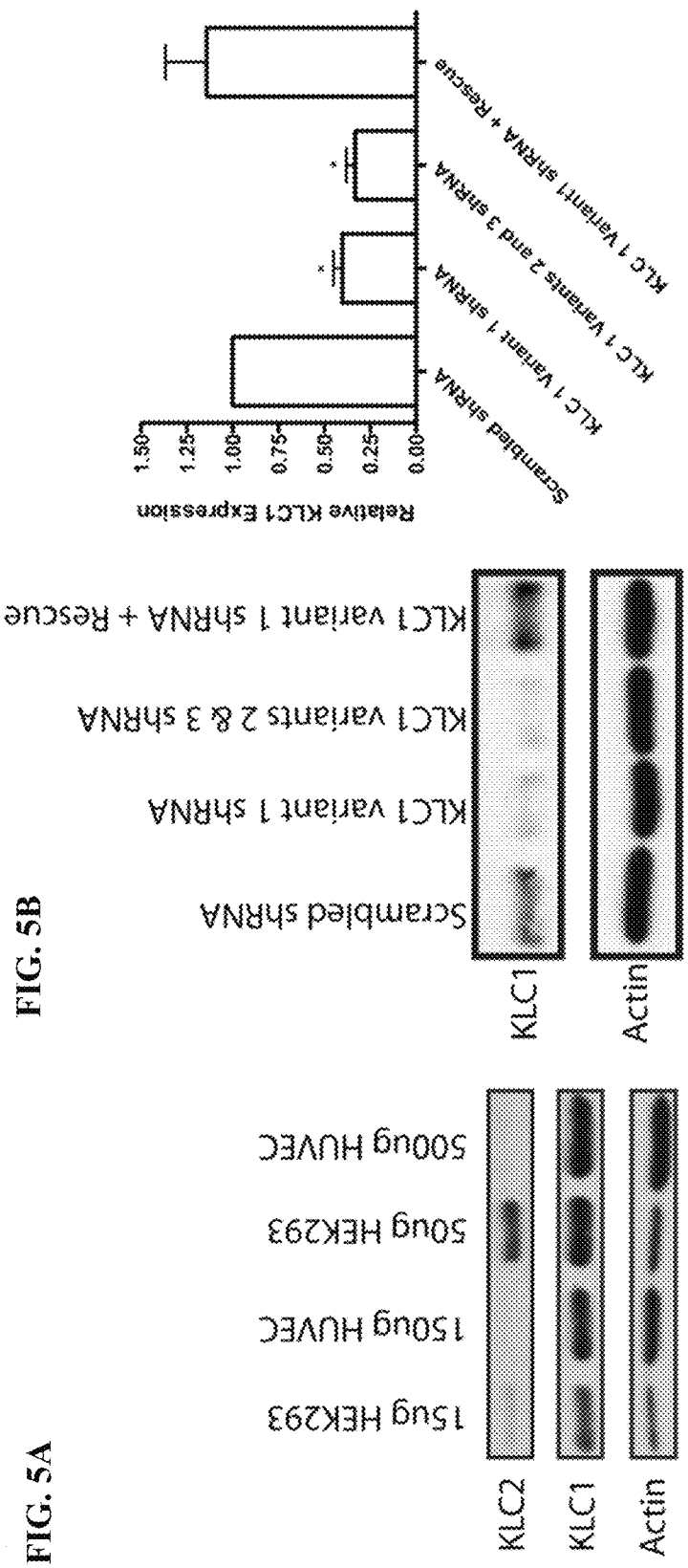
FIGS. 5A-5F. Knockdown of KLC1 isoform variant 1 in HUVEC blocks TEM. A) Western Blot analysis of KLC2 expression in HEK293 cells versus HUVEC demonstrates absence of KLC2 in HUVEC. Cells were plated on Mattek dishes and lysed 96 hours later. The amount of lysate added to the gels is indicated and was adjusted to obtain similar KLC1 expression levels in 293 cells versus HUVEC in order to fairly assess KLC2 levels in 293 cells versus HUVEC. B) HUVEC were transduced with Scrambled shRNA, KLC1 variant 1 shRNA, KLC1 variants 2 & 3 shRNA, or KLC1 variant 1 shRNA and the KLC1 variant 1 rescue construct. Cells were lysed 72 hours later. Western Blot quantified on the right. C) HUVEC were transduced with scrambled shRNA, KLC1 Variant 1 shRNA, KLC1 Variants 2 & 3 shRNA, KLC Variants 1-3 shRNA, or KLC1 Variant 1 shRNA with the KLC1 Variant 1 rescue construct. Adhesion and D) migration to cell borders were measured after an 8.5-minute TEM period. E) Monocytes or F) neutrophils were allowed to transmigrate for 60 minutes before TEM was quantified.

The potential for kinesin light chain (KLC) involvement in mediating binding between the LBRC and Kinesin-1 was examined, specifically during targeted recycling and TEM. While at least four Kinesin-1 light chains have been described or predicted (refs. 35,36; herein incorporated by reference in their entireties), KLC1 and KLC2 are the two that have been reported in the literature to interact with Kinesin-1 and can mediate cargo binding. However, KLC2 is not expressed by HUVEC (FIG. 5A), so studies focused on KLC1. KLC1 has several well-described potential splice variants (refs. 37,38; herein incorporated by reference in their entireties). We transduced HUVEC with adenovirus expressing shRNA targeting the most commonly reported specific splice variants of human KLC1, and measured a decrease in KLC1 expression compared to HUVEC transduced with scrambled shRNA (FIG. 5B). The hairpins transduced targeted variant 1 (KLC1C), variants 2 (KLC1H) and 3 (KLC1D), or all three variants.

Figure 5C:
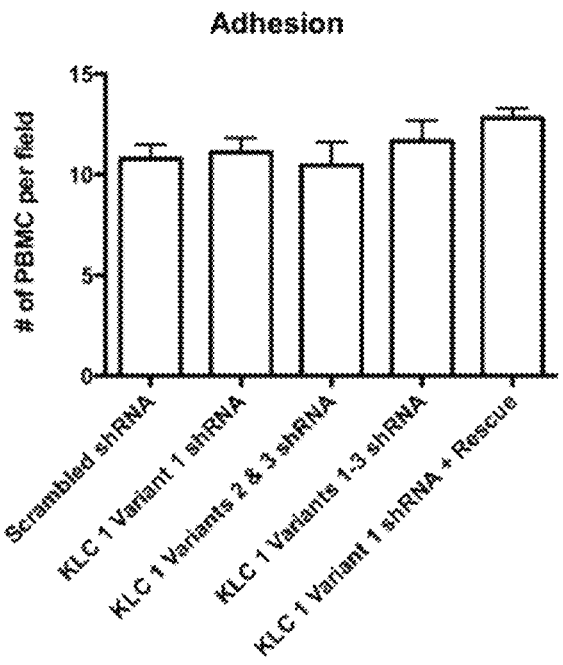
Figure 5D:
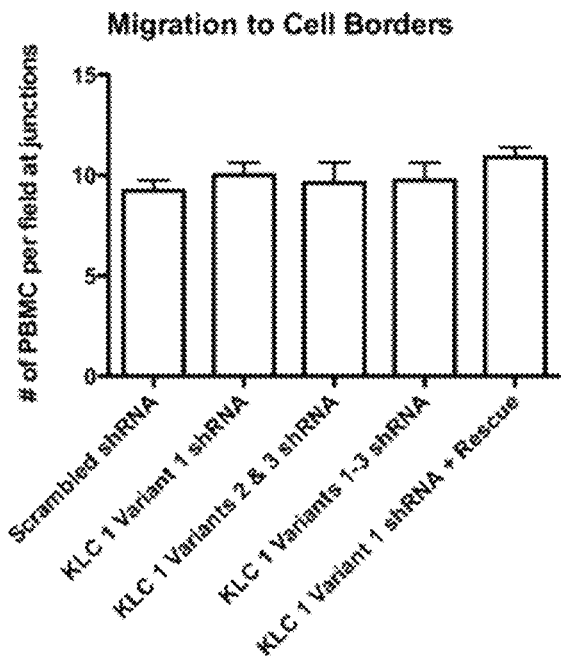
Figure 5E:
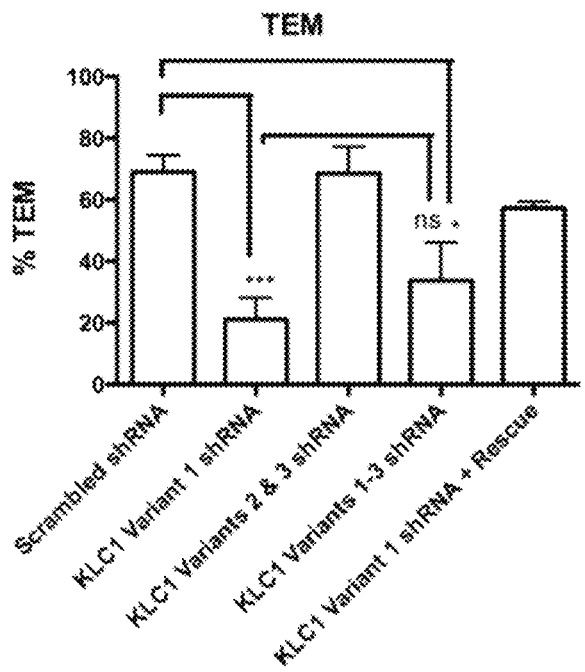
Figure 5F:
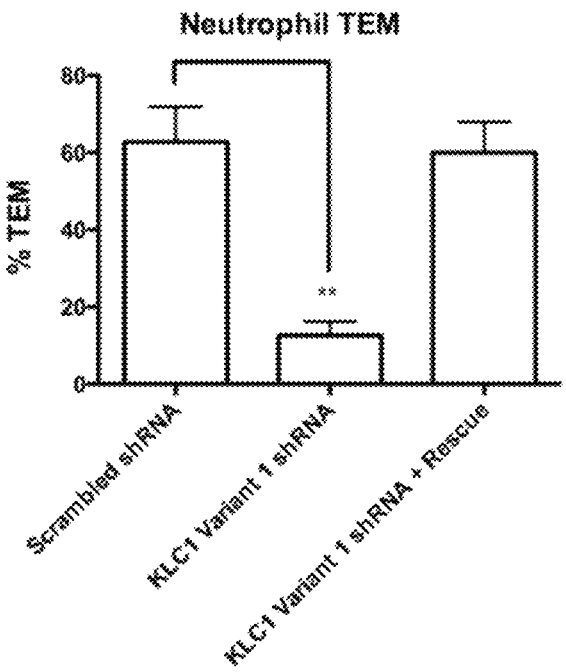

Neither adhesion (FIG. 5C) nor migration (FIG. 5D) to cell borders was affected upon transduction of any KLC shRNA construct. TEM experiments were then conducted to assess any involvement of KLC1 in this process. TEM was only reduced upon transduction with the KLC1 variant 1 shRNA construct and the shRNA simultaneously targeting variants 1, 2, and 3, but not the construct targeting just KLC1 variants 2 and 3. TEM is restored upon transduction with virus expressing KLC1 variant 1 cDNA. These data demonstrate that KLC1 variant 1 (KLC1C) is required for TEM (FIG. 5E).

Knockdown of Kinesin-1 Light Chain 1 Variant 1 Inhibits Targeted Recycling of the LBRC Upon knockdown of KLC1 isoform variant 1 in HUVEC, overall LBRC enrichment around and under adherent monocytes (FIGS. 6, A and B) as well as the percent of monocytes around which LBRC is enriched (targeted recycling, FIG. 6C) were significantly diminished, but restored to control levels upon rescue of this specific KLC1 variant. Knockdown of the other KLC1 isoform variants did not affect the level of targeted recycling.

All publications and patents mentioned herein are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

REFERENCES

The following references, some of which are cited above by number, are herein incorporated by reference in their entireties.

[1] Butcher E C: Leukocyte-endothelial cell recognition: three (or more) steps to specificity and diversity. Cell 1991, 67:1033-6.

[2] Ley K, Laudanna C, Cybulsky M I, Nourshargh S: Getting to the site of inflammation: the leukocyte adhesion cascade updated. Nat Rev Immunol 2007, 7:678-89.

[3] Muller W A: Mechanisms of leukocyte transendothelial migration. Annu Rev Pathol 2011, 6:323-44.

[4] Zen K, Parkos, C. A.: Leukocyte-epithelial interactions. Curr Opin Cell Biol 2003, 15:557-64.

[5] Mamdouh Z, Chen X, Pierini L M, Maxfield F R, Muller W A: Targeted recycling of PECAM from endothelial cell surface-connected compartments during diapedesis. Nature 2003, 421:748-53.

[6] Mamdouh Z, Kreitzer G E, Muller W A: Leukocyte transmigration requires kinesin-mediated microtubule-dependent membrane trafficking from the lateral border recycling compartment. J Exp Med 2008, 205:951-66.

[7] Feng D, Nagy J A, Hipp J, Dvorak H F, Dvorak A M: Vesiculo-vacuolar organelles and the regulation of venule permeability to macromolecules by vascular permeability factor, histamine, and serotonin. J Exp Med 1996, 183: 1981-6.

[8] Sullivan D P, Muller W A: Neutrophil and monocyte recruitment by PECAM, CD99, and other molecules via the LBRC. Seminars in immunopathology 2014, 36:193-209.

[9] Feng G, Sullivan D P, Han F, Muller W A: Segregation of VE-cadherin from the LBRC depends on the ectodomain sequence required for homophilic adhesion. Journal of cell science 2015, 128:576-88.

[10] Sullivan D P, Seidman M A, Muller W A: Poliovirus receptor (CD155) regulates a step in transendothelial migration between PECAM and CD99. Am J Pathol 2013, 182:1031-42.

[11] Mamdouh Z, Mikhailov A, Muller W A: Transcellular migration of leukocytes is mediated by the endothelial lateral border recycling compartment. J Exp Med 2009, 206:2795-808.

[12] Rodionov V I, Gyoeva F K, Gelfand V I: Kinesin is responsible for centrifugal movement of pigment granules in melanophores. Proc Natl Acad Sci USA 1991, 88:4956-60.

[13] Bloom G S, Wagner M C, Pfister K K, Brady S T: Native structure and physical properties of bovine brain kinesin and identification of the ATP-binding subunit polypeptide. Biochemistry 1988, 27:3409-16.

[14] Hirokawa N, Pfister K K, Yorifuji H, Wagner M C, Brady S T, Bloom G S: Submolecular domains of bovine brain kinesin identified by electron microscopy and monoclonal antibody decoration. Cell 1989, 56:867-78.

[15] Gindhart J G, Jr., Desai C J, Beushausen S, Zinn K, Goldstein L S: Kinesin light chains are essential for axonal transport in Drosophila. The Journal of cell biology 1998, 141:443-54.

[16] Glater E E, Megeath L J, Stowers R S, Schwarz T L: Axonal transport of mitochondria requires milton to recruit kinesin heavy chain and is light chain independent. The Journal of cell biology 2006, 173:545-57.

[17] Rice S E, Gelfand V I: Paradigm lost: milton connects kinesin heavy chain to miro on mitochondria. The Journal of cell biology 2006, 173:459-61.

[18] Muller W A, Ratti C M, McDonnell S L, Cohn Z A: A human endothelial cell-restricted, externally disposed plasmalemmal protein enriched in intercellular junctions. J Exp Med 1989, 170:399-414.

[19] Muller W A, Weigl S: Monocyte-selective transendothelial migration: Dissection of the binding and transmigration phases by an in vitro assay. J Exp Med 1992, 176:819-28.

[20] Wright S D, Rao P E, Van Voorhis W C, Craigmyle L S, Lida K, Talle M A, Westberg E F, Goldstein G, Silverstein S C: Identification of the C3bi receptor of human monocytes and macrophages by using monoclonal antibodies. Proceedings of the National Academy of Science 1983, 80:5699-703.

[21] Muller W A, Weigl S A, Deng X, Phillips D M: PECAM-1 is required for transendothelial migration of leukocytes. J Exp Med 1993, 178:449-60.

[22] Anisman H, Baines M G, Berczi I, Bernstein C N, Blennerhassett M G, Gorczynski R M, Greenberg A H, Kisil F T, Mathison R D, Nagy E, Nance D M, Perdue M H, Pomerantz D K, Sabbadini E R, Stanisz A, Warrington R J: Neuroimmune mechanisms in health and disease: 2. Disease. Cmaj 1996, 155:1075-82.

[23] Liao F, Huynh H K, Eiroa A, Greene T, Polizzi E, Muller W A: Migration of monocytes across endothelium and passage through extracellular matrix involve separate molecular domains of PECAM-1. J Exp Med 1995, 182:1337-43.

[24] Hirokawa N, Noda Y, Tanaka Y, Niwa S: Kinesin superfamily motor proteins and intracellular transport. Nat Rev Mol Cell Biol 2009, 10:682-96.

[25] Lawrence C J, Dawe R K, Christie K R, Cleveland D W, Dawson S C, Endow S A, Goldstein L S, Goodson H V, Hirokawa N, Howard J, Malmberg R L, McIntosh J R, Miki H, Mitchison T J, Okada Y, Reddy A S, Saxton W M, Schliwa M, Scholey J M, Vale R D, Walczak C E, Wordeman L: A standardized kinesin nomenclature. J Cell Biol 2004, 167:19-22.

[26] Hirokawa N: From electron microscopy to molecular cell biology, molecular genetics and structural biology: intracellular transport and kinesin superfamily proteins, KIFs: genes, structure, dynamics and functions. Journal of Electron Microscopy 2011, 60:S63-S92.

[27] Ingold A L, Cohn S A, Scholey J M: Inhibition of kinesin-driven microtubule motility by monoclonal antibodies to kinesin heavy chains. The Journal of cell biology 1988, 107:2657-67.

[28] Kanai Y, Okada, Y., Tanaka, Y., Harada, A., Terada, S., Hirokawa, N.: KIF5C, a novel neuronal kinesin enriched in motor neurons. J Neurosci 2000, 20:6374-84.

[29] Jaulin F, Xue X, Rodriguez-Boulan E, Kreitzer G: Polarization-dependent selective transport to the apical membrane by KIF5B in MDCK cells. Dev Cell 2007, 13:511-22.

[30] Krylyshkina O, Kaverina I, Kranewitter W, Steffen W, Alonso M C, Cross R A, Small J V: Modulation of substrate adhesion dynamics via microtubule targeting requires kinesin-1. The Journal of cell biology 2002, 156:349-59.

[31] Daire V, Giustiniani J, Leroy-Gori I, Quesnoit M, Drevensek S, Dimitrov A, Perez F, Pous C: Kinesin-1 regulates microtubule dynamics via a c-Jun N-terminal kinase-dependent mechanism. The Journal of biological chemistry 2009, 284:31992-2001.

[32] Cole D G, Chinn S W, Wedaman K P, Hall K, Vuong T, Scholey J M: Novel heterotrimeric kinesin-related protein purified from sea urchin eggs. Nature 1993, 366:268-70.

[33] Aizawa H, Sekine Y, Takemura R, Zhang Z, Nangaku M, Hirokawa N: Kinesin family in murine central nervous system. The Journal of cell biology 1992, 119:1287-96.

[34] Niclas J, Navone F, Hom-Booher N, Vale R D: Cloning and localization of a conventional kinesin motor expressed exclusively in neurons. Neuron 1994, 12:1059-72.

[35] Rahman A, Friedman D S, Goldstein L S: Two kinesin light chain genes in mice. Identification and characterization of the encoded proteins. The Journal of biological chemistry 1998, 273:15395-403.

[36] Junco A, Bhullar B, Tarnasky H A, van der Hoorn F A: Kinesin light-chain KLC3 expression in testis is restricted to spermatids. Biology of reproduction 2001, 64:1320-30.

[37] Khodjakov A, Lizunova E M, Minin A A, Koonce M P, Gyoeva F K: A specific light chain of kinesin associates with mitochondria in cultured cells. Mol Biol Cell 1998, 9:333-43.

[38] McCart A E, Mahony D, Rothnagel J A: Alternatively spliced products of the human kinesin light chain 1 (KNS2) gene. Traffic 2003, 4:576-80.

[39] Diefenbach R J, Mackay J P, Armati P J, Cunningham A L: The C-terminal region of the stalk domain of ubiquitous human kinesin heavy chain contains the binding site for kinesin light chain. Biochemistry 1998, 37:16663-70.

[40] Cyr J L, Pfister K K, Bloom G S, Slaughter C A, Brady S T: Molecular genetics of kinesin light chains: generation of isoforms by alternative splicing. Proceedings of the National Academy of Sciences of the United States of America 1991, 88:10114-8.

[41] Wedaman K P, Knight A E, Kendrick-Jones J, Scholey J M: Sequences of sea urchin kinesin light chain isoforms. Journal of molecular biology 1993, 231:155-8.

[42] Gindhart J G, Jr., Goldstein L S: Tetratrico peptide repeats are present in the kinesin light chain. Trends in biochemical sciences 1996, 21:52-3.

[43] Gyoeva F K, Bybikova E M, Minin A A: An isoform of kinesin light chain specific for the Golgi complex. Journal of cell science 2000, 113 (Pt 11):2047-54.

[44] Woźniak M J, Allan, Victoria J.: Cargo selection by specific kinesin light chain 1 isoforms. EMBO J 2006, 25:5457-68

[46] Liao G G G: Kinesin is a candidate for cross-bridging microtubules and intermediate filaments. Selective binding of kinesin to detyrosinated tubulin and vimentin. J Biol Chem 1998, 273:9797-803.

[48] Morihara T, Hayashi N, Yokokoji M, Akatsu H, Silverman M A, Kimura N, Sato M, Saito Y, Suzuki T, Yanagida K, Kodama T S, Tanaka T, Okochi M, Tagami S, Kazui H, Kudo T, Hashimoto R, Itoh N, Nishitomi K, Yamaguchi-Kabata Y, Tsunoda T, Takamura H, Katayama T, Kimura R, Kamino K, Hashizume Y, Takeda M: Transcriptome analysis of distinct mouse strains reveals kinesin light chain-1 splicing as an amyloid-beta accumulation modifier. Proceedings of the National Academy of Sciences of the United States of America 2014, 111:2638-43.

[47] Inomata H, Nakamura Y, Hayakawa A, Takata H, Suzuki T, Miyazawa K, Kitamura N: A scaffold protein JIP-1b enhances amyloid precursor protein phosphorylation by JNK and its association with kinesin light chain 1. The Journal of biological chemistry 2003, 278:22946-55.

[48] Kamal A, Stokin G B, Yang Z, Xia C H, Goldstein L S: Axonal transport of amyloid precursor protein is mediated by direct binding to the kinesin light chain subunit of kinesin-I. Neuron 2000, 28:449-59.

---

The invention claimed is:

1. A method of inhibiting transendothelial migration (TEM) of leukocytes within a subject comprising administering to endothelial cells of the subject an effective amount of a peptide comprising a sequence of SEQ ID NO: 4 and a cell-penetrating peptide sequence.

2. The method of claim 1, wherein inhibiting TEM reduces inflammation in the subject.

3. The method of claim 1, wherein inhibiting TEM inhibits targeted recycling of the lateral border recycling compartment (LBRC).

4. The method of claim 1, wherein the peptide is administered systemically.

5. The method of claim 1, wherein the peptide is administered locally.

6. The method of claim 1, wherein the peptide comprises a sequence of SEQ ID NO: 5.

7. The method of claim 1, wherein the peptide comprises a sequence of SEQ ID NO: 6.

8. The method of claim 1, wherein the peptide comprises a sequence of SEQ ID NO: 7.

9. The method of claim 1, wherein the peptide comprises a sequence of SEQ ID NO: 8.

10. The method of claim 1, wherein the peptide comprises a sequence of SEQ ID NO: 2.

11. The method of claim 1, wherein the cell-penetrating peptide sequence is a trans-activating transcriptional activator (TAT) peptide.

12. The method of claim 1, wherein the cell-penetrating peptide sequence is an antennapedia peptide.

* * * * *